United States Patent [19]
Ishii et al.

[11] Patent Number: 5,958,821
[45] Date of Patent: Sep. 28, 1999

[54] OXIDATION CATALYTIC SYSTEM AND OXIDATION PROCESS USING THE SAME

[75] Inventors: Yasutaka Ishii, Takatsuki; Tatsuya Nakano, Himeji, both of Japan

[73] Assignee: Daicel Chemical Industries, Ltd., Osaka, Japan

[21] Appl. No.: 08/913,881

[22] PCT Filed: Feb. 6, 1997

[86] PCT No.: PCT/JP97/00279

§ 371 Date: Sep. 24, 1997

§ 102(e) Date: Sep. 24, 1997

[87] PCT Pub. No.: WO97/28897

PCT Pub. Date: Aug. 14, 1997

[30]      Foreign Application Priority Data

| Feb. 7, 1996 | [JP] | Japan | 8-046804 |
| Feb. 7, 1996 | [JP] | Japan | 8-046805 |
| Feb. 8, 1996 | [JP] | Japan | 8-048184 |
| Feb. 9, 1996 | [JP] | Japan | 8-047920 |
| Feb. 9, 1996 | [JP] | Japan | 8-047921 |
| Feb. 11, 1996 | [JP] | Japan | 8-048188 |
| Jul. 15, 1996 | [JP] | Japan | 8-184866 |

[51] Int. Cl.[6] .................. B01J 31/12; C07D 207/404; C07D 207/448; C07D 207/12

[52] U.S. Cl. .................. 502/167; 548/545; 548/549; 548/551; 548/552; 502/152

[58] Field of Search .................. 548/545, 548, 548/549, 551, 552; 502/167, 152

[56]        References Cited

U.S. PATENT DOCUMENTS 5,030,739  7/1991  Foricher et al. .................. 552/542

FOREIGN PATENT DOCUMENTS

| 0198351A2 | 10/1986 | European Pat. Off. . |
| B-42-16621 | 9/1942 | Japan . |
| B-42-26792 | 12/1942 | Japan . |
| A-4356482 | 12/1992 | Japan . |
| A-5310610 | 11/1993 | Japan . |
| A-8217745 | 8/1996 | Japan . |

OTHER PUBLICATIONS

Ozaki, Shigeko et al., Epoxidation Catalysed by MnIIITP-PCL, J. Chem. Soc., Perkin Trans. II, pp. 951–956, Dec. 1989.

Kouichi et al, "Aerobic Oxidation Using Vanadomolyb-dophosphate ($NPV_6Mo_6$) N–Hydroxyphthalimide System", the 67th Spring Annual Meeting of Chemical Society of Japan (1994) pp. 1–4.

*Primary Examiner*—Johann Richter
*Assistant Examiner*—Dominic Keating
*Attorney, Agent, or Firm*—Birch, Stewart, Kolasch & Birch, LLP

[57]        ABSTRACT

A substrate (e.g., a cycloalkane, a polycyclic hydrocarbon, an aromatic compound having a methyl group or methylene group adjacent to an aromatic ring) is oxidized with oxygen in the presence of an oxidation catalyst comprising an imide compound of the following formula (1) (e.g., N-hydroxyphthalimide), and a co-catalyst (except phospho-vanadomolybdic acid) containing an element selected from the group consisting of Group 2A elements of the Periodic Table of Elements, transition metals (Group 3A to 7A elements, Group 8 elements, Group 1B elements and Group 2B elements of the Periodic Table of Elements) and Group 3B elements of the Periodic Table of Elements, for the formation of an oxide (e.g., a ketone, an alcohol, a carboxylic acid):

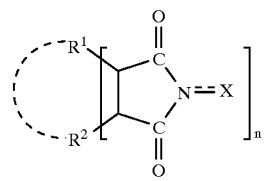

(1)

wherein $R^1$ and $R^2$ represent a substituent such as a hydrogen atom or a halogen atom, or $R^1$ and $R^2$ may together form a double bond or an aromatic or nonaromatic 5- to 12-membered ring, X is O or OH, and n is 1 to 3.

40 Claims, No Drawings

OXIDATION CATALYTIC SYSTEM AND OXIDATION PROCESS USING THE SAME

This application is 371 of PCT/JP97/00279 filed Feb. 6, 1997.

TECHNICAL FIELD

This invention relates to an oxidation catalytic system, which is useful for oxidation of a substrate with oxygen to produce a corresponding oxide with high efficiency, and to a process for oxidation (or a process for producing a ketone, an alcohol, an aldehyde or a carboxylic acid) using this catalytic system.

BACKGROUND TECHNOLOGY

An oxidation reaction is a most basic reaction in the field of industrial organic chemistry, and there are a variety of known oxidation processes, in particular an oxidation process for a substrate using nitric acid. By way of illustration, adipic acid that is a raw material for the production of nylon 66 is prepared by a process of oxidizing cyclohexanol and no other, or a mixture of cyclohexanol and cyclohexane (KA oil) with nitric acid. A long-chain dicarboxylic acid (e.g., suberic acid, azelaic acid, sebacic acid, decanedicarboxylic acid) is produced by a process of oxidizing a corresponding macrocyclic (large-ring) cycloalkane (e.g., cyclooctane, cyclononane, cyclodecane, cyclododecane) with the use of nitric acid, and such a long-chain dicarboxylic acid is employed as a raw material for the production of polyesters or polyamides.

Each of these processes, however, requires an expensive exhaust gas treatment plant for treatment of $N_2O$ and $NO_x$ produced by the oxidation with nitric acid.

In view of these problems, production processes for adipic acid by oxidative carbonylation of butadiene or carbon monoxide (CO) insertion technology have been investigated. These technologies, however, are insufficient for commercial production.

A preferred oxidation process from the viewpoints of resources and environment is a catalytic oxidation, which is conducted with direct use of molecular oxygen or air as an oxidizing agent. Therefore, there has been investigated an oxidation process, which comprises contacting a substrate catalytically and directly with molecular oxygen in the presence of a cobalt catalyst or a boric acid catalyst. By way of example, an oxidation process has been examined, which comprises direct and catalytic contact of cyclohexane, a macrocyclic cycloalkane, or other cycloalkanes or cycloalkenes with molecular oxygen in the presence of a cobalt catalyst or a boric acid catalyst. The use of the cobalt catalyst in the catalytic system, however, requires recovery of the expensive cobalt catalyst, or results in precipitation of the cobalt catalyst. Further, such a catalytic oxidation requires a high temperature and/or a high pressure for activation of oxygen, and the process has still insufficient transformation rate and selectivity. Moreover, to retain the selectivity in a high level, the production process of adipic acid requires to form adipic acid with suppressing the transformation rate or conversion at about 10%. Therefore, according to the catalytic oxidation, commercially satisfactory conversion and selectivity would not be expected in the production of an oxide (e.g., adipic acid, cyclohexenol, cyclohexene) from a corresponding substrate (e.g., cyclohexane or other cycloalkanes, cycloalkenes) under mild conditions.

As for oxidation of a macrocyclic cycloalkane, Japanese Patent Publication No. 3100/1968 (JP-B-43-3100) discloses a production process of lactam, which is used as a raw material for the production of nylon 12. This process comprises the steps of oxidizing cyclododecane with air in the presence of a boric acid catalyst, dehydrogenating cyclododecanol of the products to give cyclododecanone, and reacting cyclododecanone with nitrosylsulfuric acid by Beckmann's rearrangement. However, the macrocyclic cycloalkane is stabler and less reactive than cyclohexane. Accordingly, the conversion of cyclododecane is so small, in the above oxidation process using air, that a yield of cyclododecanone is still insufficient even inclusive of cyclododecanol. In particular, according to the catalytic oxidation commercial production of an oxide (e.g., a carbonyl compound or a carboxylic acid) would not be expected with high yield and high efficiency from a corresponding macrocyclic cycloalkane under mild or moderate conditions.

Incidentally, an attempt has been made for oxidation of a substrate using a radical initiator such as azobisisobutyronitrile in the presence of oxygen, as well. According to this technology, however, it is difficult to produce an oxidized compound from a corresponding cycloalkene with high selectivity and a good yield.

On the other hand, a polycyclic hydrocarbon having a carbon-hydrogen bond (methylidyne group) in a fusing or junction site of adjacent rings or in a bridgehead position can be prepared by hydrogenation and thermal conversion (thermal transfer) of a polycyclic aromatic compound (e.g., naphthalene, acenaphthene, anthracene, phenanthrene, phenalene, or alkyl-substituted derivatives of these compounds) at a high temperature under a high pressure [Japanese Patent Publication No. 2909/1977 (JP-B-52-2909), Japanese Patent Publication No. 12706/1977 (JP-B-52-12706), Japanese Patent Publication No. 35942/1978 (JP-B-53 -35942), Japanese Patent Publication No. 35944/1978 (JP-B-53-35944), Japanese Patent Application Laid-open No. 246333/1985 (JP-A-60-246333)]. Such a polycyclic aromatic compound is available abundantly in purification process of petroleum. The polycyclic hydrocarbon as prepared in such a technology is thermally stable and thus employed as a higher lubricating oil, which requires heat resisting property.

The polycyclic hydrocarbons respectively have skeletons, which insure mutual stabilization of each ring, such as adamantane and other compounds having a three-dimensionally symmetric structure, and, as a result, endowed with distinctive functions. Thus, various copolymers each having enhanced or improved function or characteristics can be obtained by introducing a hydroxyl group into such polycyclic hydrocarbons and, if necessary, inducing them into an acrylic acid derivative or a carbonate. In a bridged cyclic hydrocarbon having a methine-carbon atom in a bridgehead position, there have been proposed various production processes for obtaining such copolymers from a functional group-introduced adamantane. The processes include, for example, a process of producing a polyester [Japanese Patent Publication No. 26792/1967 (JP-B-42-26792), Japanese Patent Publication No. 937/1968 (JP-B-43-937), Japanese Patent Publication No. 34628/1971 (JP-B-46-34628), Japanese Patent Application Laid-open No. 21090/1975 (JP-A-50-21090)], a process of producing a polycarbonate [U.S. Pat. No. 3,516,969, U.S. Pat. No. 3,594,427], a process for producing a polyamide or a polyimide [Japanese Patent Publication No. 2024/1970 (JP-B-45-2024), U.S. Pat. No. 3,832,332, U.S. Pat. No. 3,814,735], a process for producing a polyurethane [Japanese Patent Publication No. 700/1968 (JP-B-43-700), Japanese Patent Publication No. 6456/1968 (JP-B-43-6456), Japanese Patent Publication No. 6267/1969 (JP-B-44-6267), Japanese Patent Publication No. 12891/1969 (JP-B-44-12891)], a process for producing a polysulfone and a polysulfonate [U.S. Pat. No. 3,738,960, U.S. Pat. No. 3,738,965, U.S. Pat. No. 3,753,950], and a process for producing a vinyl polymer [Japanese Patent Publication No. 36950/1970 (JP-B-45-36950), Japanese Patent Publication No. 28419/1971 (JP-B-46-28419)]. Further, a homopolymer as produced using a polycyclic hydrocarbon as a monomer has also been proposed (U.S. Pat. No. 3,649,702).

Polymers each containing such a polycyclic hydrocarbon have generally excellent functions or characteristics (high functionality). They have, for example, excellent heat resistance (heat resisting property), moisture resistance, small light-inducing loss, high refractive index, double refraction index and other optical characteristics, coefficient of thermal expansion and other characteristics. Such excellent characteristics cannot be achieved with the use of conventional polymers. Accordingly, their applications have been investigated for optical fibers, optical elements, optical lenses, hologram, optical discs, contact lenses and other optical materials, transparent resin coating compositions for organic glasses, electric conductive polymers, photosensitive materials, fluorescent materials and so forth.

Incidentally, an amino derivative derived from an alcohol of a bridged cyclic hydrocarbon is useful for introducing various pharmaceuticals and/or agricultural chemicals each having excellent pharmacological activity, such as "SYMMETREL" (a trade name) as a therapeutic agent for Parkinson's disease, typically speaking. By way of example, adamantane, hemiadamantane, norbornene, tetralin and their derivatives are used for such applications.

As described above, polycyclic hydrocarbons each having a functional group in a bridgehead position are compounds applicable to many applications, and most of these compounds may be induced or derived from corresponding alcohols. In particular, polyols each substituted with hydroxyl groups on plural, i.e., two or more bridgehead positions can be advantageously employed for production of progressive materials (highly functional materials). However, it is difficult to introduce hydroxyl groups into the bridgehead positions of such chemically stable polycyclic hydrocarbons with effectiveness and high efficiency. By way of illustration, introduction of hydroxyl groups is conducted by bromination of a bridged cyclic hydrocarbon (e.g., adamantane or its derivative) with the use of excess bromine (e.g., 10 times by mole or more), and hydrolyzing the formed bromide with silver nitrate or silver sulfate in an excess amount greater than a stoichiometric amount (Chem. Ber., 92, 1629 (1959), 93, 226, 1161 (1960): J. Org. Chem., 26 2207 (1961)).

In this process, however, the reaction should be conducted over a long period at a temperature of about 100° C. using a large quantity of bromine. Besides, the reaction consumes the expensive silver reagent in a large quantity. Moreover, successive bromination of two or more bridgehead positions would not be expected. Therefore, a catalyst such as boron tribromide and aluminum tribromide is required when adamantane is employed in the process. In the bromination process, loss in the hydrolysis step is so great that the recoveries of an adamantanemonool and an adamantanediol are at most 81% and 57%, respectively, in terms of the produced alcohols. In addition, since an adamantanetriol cannot be formed directly from adamantane, it has to be produced by isolation and hydrolysis of a successively highly brominated compound. Accordingly, the yield of the adamantanetriol is extremely low at about 10 to 30% [Tetrahedron Letters, 19 1841 (1967); Just. Liebigs Ann. Chem., 717 60 (1968)].

As a process for producing an adamantanediol, there has been known an oxidation process using chromic acid as well. For example, Japanese Patent Publication No. 16621/1967 (JP-B-42-16621) discloses that an adamantanediol is obtained in a yield of 96% and selectivity of 96% by reacting adamantane with five times by mole or more of chromic acid in a concentrated acetic acid solution at a temperature of 90° C. This technology is useful for oxidation of a bridgehead of a polycyclic hydrocarbon to form an alcohol derivative. However, this technology requires an excessive amount of expensive chromic acid. Such a reagent is highly toxic, and in addition, an after-treatment and/or recovery equipment is required. Therefore, the process is disadvantageous in commercial production. Moreover, an excess amount of sulfuric acid is necessary in addition to chromic acid. Furthermore, it is necessary to control the reaction temperature and the concentration of acetic acid as a solvent, so that the process would not have excellent reaction workability. Further, although an adamantanediol is formed according to the process, oxidation of adamantane to a triol or higher polyol will not proceed, even when the reaction is carried out in severe conditions.

Regarding a catalytic oxidation in which molecular oxygen or air is directly used as an oxidizing agent, Japanese Patent Publication No. 26792/1967 (JP-B-42-26792) describes, for instance, a process that comprises heating adamantane at oxygen pressure of 7 kg/cm$^2$ at 170° C. in the presence of a catalytic amount of cobalt naphthenate and without a solvent, and ceasing the reaction when a transformation rate of adamantane reaches 70%. The reaction mixture obtained in such a process comprises an adamantanemonool oxidized in a bridgehead position in a yield of 41%, but it contains an adamantanediol merely in a trace amount. Still more, when the heating is continued until the transformation rate of adamantane reaches 99%, the reaction not only provides adamantanediols in a yield of 25% but also by-produces a large quantity of ketone derivatives formed as a result of isomerization and oxidation. Therefore, the intended compound can hardly be isolated and purified from the reaction products.

As thus described, it is difficult to produce a polyol such as a diol, in particular triol, tetraol, or a higher polyol with high effectiveness and efficiency inhibiting production of a ketone in the production of a polycyclic hydrocarbon such as adamantane. In particular, it is difficult to prepare the polyol in mild conditions with a high transformation rate and excellent selectivity. Meanwhile, such a polycyclic hydrocarbon is useful for impartment of excellent functions.

Japanese Patent Application Laid-open No. 310610/1993 (JP-A-5-310610) discloses the results of investigations with respect to other metal species than the cobalt as a catalyst for oxidation with air. The catalysts described in the literature, however, have insufficient catalytic activities, and hence it is difficult to obtain an oxidized compound from a corresponding polycyclic hydrocarbon with high selectivity and an excellent yield.

Incidentally, the compounds, which are substituted with a hydroxyl group on a tertiary carbon atom of a junction site where adjacent rings bond each other, are useful as physiologically active substances. They have excellent utilizing values as antivirus agents, antibacterial or antifungal agents, plant hormones or the like. Further, compounds having a functional group bonded to a carbon atom of a junction position of rings are widely employed as raw materials for the production of various perfumes and fragrant compounds. Therefore, such tertiary alcohols each having a hydroxyl group in a junction position of rings are important compounds. However, when a compound having a methylidyne group in a junction site of adjacent rings is oxidized, the junction position of the adjacent rings oxidatively cleaves to form a corresponding diketone as a main product. Accordingly, it is difficult to introduce a hydroxyl group into the junction position of the rings and inhibit the formation of diketones at the same time. Consequently, a special technology with the use of substrate-specificity is employed to obtain tertiary alcohols.

By way of illustration, Japanese Patent Publication No. 5894/1987 (JP-B-62-5894) discloses a process for producing hexahydroindanol having a tertiary hydroxyl group by ring-opening epoxytetrahydroindane. The epoxytetrahydroindane has been produced by epoxidation of tetrahydroindane with the use of an aluminum alkoxide catalyst. Such hexahydroindanol and its derivatives give out fragrance or aroma, for example, like a leaf, green, camphor, ligneous, patchouli, musk, root, vervet, American carrot, pine root, soil and the like. Therefore, these compounds are used as fragrance or perfumes for various materials for the production of cologne, foods, tobacco products and so on. However, the production of the hexahydroindanol requires partial hydrogenation step of indene to give tetrahydroindane and an epoxidation step of the produced tetrahydroindane. Further, the selectivity in each reaction step is so low that the yield of an object compound is extremely small as a whole inclusive of a ring-opening step of the epoxy compound. Therefore, use of indene, as a raw material, which is available at a comparatively low cost, still fails to provide an object compound with economic advantages.

Japanese Patent Publication No. 42972/1980 (JP-B-55-42972) discloses the production of 1-hydroxytricyclo[4.3.1.1$^{2,5}$]undecane by hydrolysis of 1-halogenotricyclo[4.3.1.1$^{2,5}$]undecane. The 1-hydroxytricyclo[4.3.1.1$^{2,5}$]undecane is employed as a raw material for the production of a pharmacologically active compound, such as an amino compound having strong anti-virus activity. In Japanese Patent Application Laid-open No. 13760/1976 (JP-A-51-13760), 1-halogenotricyclo[4.3.1.1$^{2,5}$]undecane is prepared by bromination of tricyclo[4.3.1.1$^{2,5}$]undecane. The yield of the bromide is, however, only about 65%, and the yield of the amino compound inclusive of an amination step is lower than 60%. Further, since a corresponding chloride cannot be induced directly from tricyclo[4.3.1.1$^{2,5}$]undecane, it 2 is formed by reacting 1-hydroxytricyclo[4.3.1.1$^{2,5}$]undecane with an acyl chloride. As described above, tricyclo[4.3.1.1$^{2,5}$]undecane has a plenty of positions that can be oxidized, i.e., two junction sites in which the adjacent rings bond each other, two bridgehead positions, and seven methylene positions. Accordingly, direct introduction of a hydroxyl group would not be expected with high selectivity according to a conventional oxidation technology such as oxidation with chromic acid or oxidation with air.

Japanese Patent Publication No. 114538/1982 (JP-B-57-114538) discloses the preparation of 2-endohydroxyexotricyclo[5.2.1.0$^{2,6}$]decane by treating exotricyclo[5.2.1.0$^{2,6}$]decane with an organic peroxide. This alcohol is a fragrant substance having a strong aroma or fragrance like woody camphor, and is a physiologically active substance having antivirus activity, antifungal or antimicrobial activity and plant hormone activity. Such characteristics are also found in 2-hydroxyendotricyclo[5.2.2.0$^{2,6}$]undecane as produced by treating endotricyclo[5.2.2.0$^{2,6}$]undecane with an organic peroxide [Japanese Patent Publication No. 114539/1982 (JP-B-57-114539)]. However, according to the oxidation with a peroxide, the yield of the object compound is so low at about 20 to 50%. Incidentally, the endotricyclo[5.2.2.0$^{2,6}$]undecane can easily be obtained as a derivative of dicyclopentadiene [Japanese Patent Publication No. 36748/1976 (JP-B-51-36748); Synth. Comm., 4, 225 (1974)].

As described above, it is also difficult to introduce a hydroxyl group easily and effectively into a tertiary carbon atom in the junction site, where adjacent rings bond or fuse each other, in a polycyclic hydrocarbon, while inhibiting ring-opening and by-production of a diketone.

Further, an aromatic compound having a carboxyl group (e.g., benzoic acid) has been produced by a process that comprises oxidizing an aromatic compound having a methyl group (e.g., toluene) with nitric acid or dichromic acid. Such a process is useful for production of an aromatic compound having a carboxyl group, such as benzoic acid, with a comparatively high yield. The oxidation process with nitric acid, however, requires expensive equipment for treating exhaust gas, i.e., produced $N_2O$ and $NO_x$. Similarly, the oxidation process with dichromic acid requires treatment of a chromium component.

Regarding production processes of benzoic acid using oxidation with air, there have been known a process that comprises oxidizing toluene in a liquid phase with the use of cobalt naphthenate. A process that comprises oxidizing toluene in a liquid phase in the presence of a catalytic system containing cobalt-manganese acetate and a bromide is also known. However, the process using cobalt naphthenate has insufficient transformation rate and selectivity, so that efficient production of benzoic acid would not be expected. On the other hand, the process using cobalt-manganese acetate provides benzoic acid with a comparatively high yield. The reaction according to this technology, however, needs to be conducted at a comparatively high temperature (for example, about 150 to 250° C.). Therefore, it is difficult to efficiently produce a carboxylic acid from a corresponding aromatic hydrocarbon having a methyl group, inclusive of toluene, by means of oxidation with oxygen in mild or moderate conditions.

Terephthalic acid can be prepared at a comparatively low temperature (e.g., about 90 to 160° C.) by oxidizing other aromatic compound such as p-xylene with air in the presence of cobalt acetate and a co-oxidizing agent. In this process, however, not only the catalyst should be circulated in a large quantity, but also acetic acid is by-produced in an equimole amount with terephthalic acid.

Butenediol has been employed as a raw material (starting material) for the production of polyamide and other synthetic resins, maleic anhydride, and plasticizers. Further, butanediol introduced from butenediol is useful, for example, as a raw material for the production of tetrahydrofuran, butyrolactone, polyester or polyurethane. The butenediol or butanediol can be obtained by preparing butynediol with the use of Reppe reaction and hydrogenating the produced butynediol using a reduction catalyst.

On the other hand, conjugate diene such as butadiene is produced in a large quantity in petroleum purification steps. Accordingly, it is commercially useful to directly produce an alkenediol such as butenediol from a corresponding conjugate diene such as butadiene. As for a production process of a diol from a conjugate diene, it is possible to oxidize a conjugate diene with nitric acid to give a corresponding diol. As described above, however, the technology requires expensive equipment for the treatment of $N_2O$ and $NO_x$ as formed by oxidation with nitric acid. Therefore, such a process is more useful from the viewpoints of resource and environment that provides an alkenediol efficiently by a catalytic oxidation technology directly using molecular oxygen or air as an oxidizing agent. Further, this oxidation technology using oxygen or air as an oxidizing agent would be greatly useful if such an oxidation process is effective in oxidation of other conjugate compounds than the conjugate diene, e.g., oxidation of an α,β-unsaturated bond of acrylic acid or its derivative to give a corresponding oxide efficiently.

However, according to oxidation with oxygen, in particular oxidation with oxygen in mild condition, it is difficult to produce a diol or its derivative (e.g., an alkenediol, acetal) from a corresponding conjugate diene, acrylic acid or its derivative, or other conjugate compounds with high selectivity and an excellent yield.

In page 762 of the "Lecture Draft II" (1994) of 67th Spring Annual Meeting of Chemical Society of Japan, it is reported that oxidation of an alcohol such as benzyl alcohol or benzhydrol with air using vanadomolybdophosphoriate and N-hydroxyphthalimide provides a ketone such as acetophenone or benzophenone in a high yield, and that oxidation of tetralin, isochroman or adamantane with oxygen using N-hydroxyphthalimide gives a corresponding monoalcohol or monoketone.

It is, therefore, an object of the present invention to provide an oxidation catalyst which insures efficient oxidation of a substrate by means of oxidation with oxygen, and which does not particularly require treatment of exhaust gas, and an oxidation process using this catalyst.

It is another object of the invention to provide an oxidation catalyst that provides an oxide (e.g., ketone, alcohol, aldehyde, a carboxylic acid) with a high transformation rate or conversion and selectivity from a corresponding substrate (e.g., cycloalkane, cycloalkene, polycyclic hydrocarbon, an alkyl group-substituted aromatic compound, a conjugate compound) by means of oxidation with molecular oxygen, an oxidation process using this catalyst, and a production process of the oxide.

A further object of the invention is to provide an oxidation catalyst, which insures direct and efficient production, with high transformation rate and selectivity, of a carboxylic acid (e.g., adipic acid or other long-chain dicarboxylic acids, and aromatic carboxylic acids) or a ketone (e.g., cycloalkane, cycloalkenone, aromatic ketone) from a corresponding substrate (e.g., a cycloalkane, a cycloalkene, an alkyl-substituted aromatic compound) by means of contact with oxygen in mild or moderate conditions, an oxidation process with the use of this catalyst, and a production process of the carboxylic acid or ketone.

It is yet another object of the invention to provide an oxidation catalyst, which provides efficient oxidation with oxygen of a methylidyne group in a bridgehead position or junction position of a polycyclic hydrocarbon, and an oxidation process using this catalyst.

A further object of the invention is to provide an oxidation catalyst that provides a diol or higher polyol from a corresponding condensed polycyclic hydrocarbon or a bridged (cross-linked) cyclic hydrocarbon with high transformation rate and selectivity, and an oxidation process using this catalyst.

It is still another object of the invention to provide an oxidation catalyst and an oxidation process, both of which insure efficient introduction of a hydroxyl group into a tertiary carbon atom of the junction position of a polycyclic hydrocarbon in mild conditions while suppressing cleavage of the ring of the polycyclic hydrocarbon and by-production of a diketone.

A still further object of the invention is to provide a process for producing an adamantanepolyol, which provides, with effectiveness and a high yield, an adamantanediol, adamantanetriol or higher adamantanepolyol by means of oxidation with oxygen in mild conditions.

DISCLOSURE OF THE INVENTION

The present inventors did much investigation to accomplish the above objects, and as a result, found that oxidation of a substrate with oxygen or air in the presence of a catalytic system comprising an N-hydroxyphthalimide compound and a co-catalyst insures efficient oxidation even in comparatively mild conditions at ambient pressure, and therefore provides a corresponding oxide with high selectivity in a high yield. The present invention has been accomplished based on the above findings.

Thus, the oxidation catalytic system of the present invention comprises an imide compound shown by the formula (I),

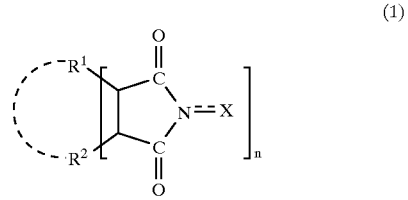

wherein $R^1$ and $R^2$ respectively represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond, or an aromatic or non-aromatic ring; X represents an oxygen atom or a hydroxyl group; n denotes an integer of 1 to 3; and a bond between N and X represents a single bond or double bond, and a co-catalyst except phosphovanadomolybdic acid. The co-catalyst includes co-catalysts each containing an element selected from the group consisting of Group 2A elements of the Periodic Table of Elements, transition metals and Group 3B elements of the Periodic Table of Elements.

The oxidation catalytic system comprising the imide compound (1) and the co-catalyst insures efficient oxidation of various substrates and provides corresponding ketones, aldehydes, alcohols or carboxylic acids. Therefore, according to the process of the invention, a substrate contacts oxygen in the presence of the oxidation catalytic system comprising the imide compound (1) and the co-catalyst.

When the substrate is a compound selected from (a) a cycloalkane, (b) a cycloalkene, (c1) a polycyclic hydrocarbon having a methylidyne group as a constitutive unit of the ring except adamantane, (d1) an aromatic compound having at least one alkyl group among other aromatic compounds, or (e) a conjugate compound, the substrate may be oxidized in the presence of an oxidation catalyst composed of the imide compound (1) without the use of the co-catalyst.

When the substrate is oxidized with oxygen in the coexistence of the co-catalyst (i.e., in the presence of the oxidation catalytic system comprising the imide compound (1) and co-catalyst), and when the substrate is an aromatic compound having a hydroxyl group in the benzyl position, the co-catalyst is not phosphovanadomolybdic acid. To be specific, when the co-catalyst is a polyacid (a heteropolyacid or an isopolyacid) comprising a Group 5A element or Group 6A element of the Periodic Table of Elements, the polyacid is generally an isopolyacid. In case the substrate is (a) the cycloalkane, (b) the cycloalkene, (c1) the polycyclic hydrocarbon except adamantane, (d1) the aromatic compound having at least one alkyl group, or (e) the conjugate compound, phosphovanadomolybdic acid may be employed as the heteropolyacid. That is, in such a case, at least one member selected from the group consisting of the oxides, organic acid salts, inorganic acid salts, halides, complexes, isopolyacids or their salts, and heteropolyacids or their salts can be used as the co-catalyst.

In a preferred embodiment of the oxidation process, use is made of a compound, as the co-catalyst, which contains an element selected from the group consisting of the Group 2A elements, transition metals and the Group 3B elements of the Periodic Table of Elements and is selected from an oxide, an organic acid salt, an inorganic acid salt, a halide, a complex, and an isopolyacid or its salt.

The invention also discloses a process for producing a ketone, an alcohol, an aldehyde or a carboxylic acid by oxidizing the substrate in the presence of the oxidation catalyst comprising the imide compound (1), or the oxidation catalytic system comprising the imide compound (1) and the co-catalyst. Further, the invention discloses the use of the oxidation catalyst comprising the imide compound (1), or the use of the oxidation catalytic system comprising the imide compound (1) and the co-catalyst, each for oxidation of the substrate.

It should be understood that the term "carboxylic acid" as used in this specification means and includes not only compounds each having a free carboxyl group but also derivatives of carboxylic acids being substantially equivalent to the carboxylic acids, such as salts, esters or acid anhydrides which form according to reaction conditions.

The adamantane and its derivative may be simply called "the adamantane component." In the polycyclic hydrocarbon, the methylidyne group in a bridgehead position is shown by the group "—HC<," and the methylidyne group in a junction position (a fusing site) of adjacent rings may be shown by the group ">CH—CH<." The term "the divalent transition metal compound" includes transition metal compounds that have formed in the reaction system, as well.

Further, the term "acrylic acid, methacrylic acid or their derivatives" may generically be referred to as "(meth)acrylic acid or its derivative." The term "conjugate compound" used in the specification means and includes compounds each having a double bond and a single bond by turns (e.g., butadiene), and compounds each having unsaturated bonds (a double bond and a triple bond) by turn with or without an interposition of a single bond (e.g., a conjugate polyene). Therefore, as far as an unsaturated diol is an oxide corresponding to "the conjugate diene," such unsaturated diol having one double bond, and that having a plurality of double bonds or triple bonds may be generically called "the alkenediol."

BEST MODES FOR PRACTICING THE INVENTION

Imide compound

In the compound shown by the formula (1), the halogen atom, as the substituents $R^1$ and $R^1$, includes iodine, bromine, chlorine and fluorine atoms. The alkyl group includes, for example, methyl, ethyl, propyl, isopropyl, butyl, isobutyl, sec-butyl, t-butyl, pentyl, hexyl, heptyl, octyl, decyl, or other straight chain or branched chain alkyl groups each having about 1 to 10 carbon atoms. An illustrative preferred alkyl group includes alkyl groups each having about 1 to 6 carbon atoms, in particular lower alkyl groups each having about 1 to 4 carbon atoms.

As the aryl group, there may be mentioned, for instance, a phenyl group and a naphthyl group. Examples of the cycloalkyl group include cyclopentyl, cyclohexyl, and cyclooctyl groups. The alkoxy group includes, for example, methoxy, ethoxy, propoxy, isopropoxy, butoxy, isobutoxy, t-butoxy, pentyloxy, hexyloxy, and other alkoxy groups each having about 1 to 10 carbon atoms. Among them, alkoxy groups each having about 1 to 6 carbon atoms, in particular lower alkoxy groups each having about 1 to 4 carbon atoms are desirable.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. A preferred alkoxycarbonyl group includes those each having about 1 to 6 carbon atoms in the alkoxy moiety, among which lower alkoxycarbonyl groups each having about 1 to 4 carbon atoms in the alkoxy moiety are typically desirable.

The acyl group includes, for instance, formyl, acetyl, propionyl, butyryl, isobutyryl, valeryl, isovaleryl, pivaloyl, and other acyl groups each having about 1 to 6 carbon atoms.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, but it may practically be a hydrocarbon ring. As such a ring, there may be mentioned, for instance, non-aromatic alicyclic rings (e.g., cyclohexane ring and other cycloalkane rings which may have a substituent, cyclohexene ring and other optionally substituted cycloalkene rings), non-aromatic bridged (cross-linked) rings (e.g., 5-norbornene ring and other optionally substituted bridged hydrocarbon rings), benzene ring, naphthalene ring and other optionally substituted aromatic rings. The ring may practically comprise an aromatic ring.

A preferred imide compound includes compounds shown by the following formula,

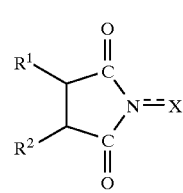

(1a)

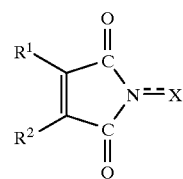

(1b)

-continued

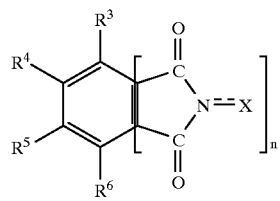

(1c)

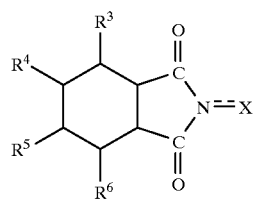

(1d)

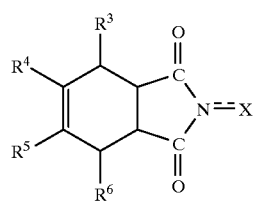

(1e)

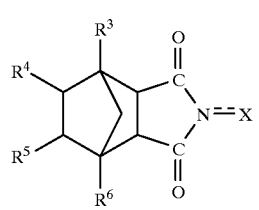

(1f)

wherein $R^3$, $R_4$, $R^5$ and $R^6$ independently represent a hydrogen atom, an alkyl group, a hydroxyl group, an alkoxy group, a carboxyl group, an alkoxycarbonyl group, an acyl group, a nitro group, a cyano group, an amino group or a halogen atom; the bond between the nitrogen atom "N" and "X" denotes a single bond or a double bond; and $R^1$, $R^2$ and n have the same meanings as defined above.

In the substituents $R^3$, $R^4$, $R^5$ and $R^6$, the alkyl group includes alkyl groups similar to those exemplified above, in particular alkyl groups each having about 1 to 6 carbon atoms. The alkoxy group includes the same alkoxy groups as mentioned above, in particular lower alkoxy groups each having about 1 to 4 carbon atoms. Examples of the alkoxycarbonyl group include the same alkoxycarbonyl groups as exemplified above, in especial lower alkoxycarbonyl groups each having about 1 to 4 carbon atoms in the alkoxy moiety. As the acyl group, there may be mentioned the similar acyl groups to those mentioned above, in particular acyl groups each having about 1 to 6 carbon atoms. Examples of the halogen atom include fluorine, chlorine and bromine atoms. The substituents $R^3$, $R^4$, $R^5$ and $R^6$ may practically be hydrogen atoms, lower alkyl groups each having 1 to 4 carbon atoms, carboxyl groups, nitro groups or halogen atoms, respectively.

The symbol X in the formula (1) denotes an oxygen atom or a hydroxyl group. A bond between the nitrogen atom "N" and "X" is a single bond or a double bond. Further, n usually denotes about 1 to 3, preferably 1 or 2. The imide compound shown by the formula (1) can be used singly or in combination in the oxidation reaction.

As examples of the acid anhydride corresponding to the imide compound of the formula (1), there may be mentioned succinic anhydride, maleic anhydride, or other saturated or unsaturated aliphatic dicarboxylic acid anhydrides, tetrahydrophthalic anhydride, hexahydrophthalic anhydride (1,2-cyclohexanedicarboxylic anhydride), 1,2,3,4-cyclohexanetetracarboxylic acid 1,2-anhydride, and other saturated or unsaturated nonaromatic cyclic polycarboxylic acid anhydrides (alicyclic polycarboxylic anhydrides), hetic anhydride, himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8:4,5-naphthalenetetracarboxylic dianhydride, and other aromatic polycarboxylic anhydrides.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellitimide, N,N'-dihydroxypyromellitimide, N,N'-dihydroxynaphthalenetetracarboximide and so forth. A typically preferable imide compound includes an N-hydroxyimide compound derived from an alicyclic polycarboxylic anhydride, in particular from an aromatic polycarboxylic anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

These imide compounds have high oxidizing activities, and catalytically promote oxidation of the specific substrate even in mild or moderate conditions. Further, when various substrates are oxidized in the coexistence of the imide compound and the co-catalyst, transformation rate and selectivity are improved. Therefore, according to the present invention, the specific substrate is oxidized in the presence of the oxidation catalyst comprising the imide compound to give a corresponding ketone, alcohol, aldehyde or carboxylic acid. Moreover, this invention provides efficient oxidation of the substrate with high selectivity in the presence of the catalytic system composed of the imide compound and the co-catalyst to form a ketone, alcohol, aldehyde or carboxylic acid corresponding to the substrate.

Co-catalyst

A co-oxidizing agent as the co-catalyst includes or comprises metal compounds such as compounds each comprising or containing a Group 2A element of the Periodic Table of Elements (e.g., magnesium, calcium, strontium, barium), a transition metal compound, or a boron compound or other compounds containing a Group 3B element (e.g., boron B, aluminium Al) of the Periodic Table of Elements. These co-catalysts may be employed independently or in combination.

As the elements of the transition metal, there may be mentioned, for instance, Group 3A elements of the Periodic Table of Elements (e.g., scandium Sc, yttrium Y, and lanthanum La, cerium Ce, samarium Sm and other lanthanoid elements, actinium Ac and other actinoid elements), Group 4A elements of the Periodic Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2B elements of the Periodic Table of Elements (e.g., zinc Zn, cadmium Cd).

A preferred element constituting the co-catalyst includes elements of the transition metals (e.g., lanthanoid elements, actinoid elements and other Group 3A elements of the Periodic Table of Elements, Group 4A elements, Group 5A elements, Group 6A elements, Group 7A elements, Group 8 elements, Group 1B elements, and Group 2B elements of the Periodic Table of Elements) and Group 3B elements of the Periodic Table of Elements (e.g., boron compounds). In particular, high oxidizing activities are demonstrated when the imide compound of the formula (I) is used in combination with a compound containing containing Ti, Zr or other Group 4A elements, V or other Group 5A elements, Cr, Mo, W or other Group 6A elements, Mn, Tc, Re or other Group 7A elements, Fe, Ru, Co, Rh, Ni or other Group 8 elements, or Cu or other Group 1B elements.

The species of the co-catalyst is not particularly limited as far as it contains the element and has oxidizing property, and it may be a simple substance or hydroxide of a metal. The co-catalyst, however, may practically be an oxide of a metal (a double oxide or an oxygen acid salt), an organic acid salt, an inorganic acid salt, a halide, each of which contains the element, a coordinate compound (a complex), a heteropolyacid (in particular, an isopolyacid) or its salt, each of which contains the metal element. In the oxidation catalytic system comprising the co-catalyst in combination with the imide compound of the formula (1), phosphovanadomolybdic acid is excluded from compounds each containing the Group 5A element or the Group 6A element of the Periodic Table of Elements.

As the boron compound, there may be mentioned, for example, a boron hydride (e.g., borane, diborane, tetraborane, pentaborane, decaborane), a boric acid (e.g., orthoboric acid, metaboric acid, tetraboric acid), a borate (e.g., a nickel borate, magnesium borate, manganese borate), $B_2O_3$, and other boron oxides, borazane, borazene, borazine, boron amide, boron imide, and other nitrogen-containing boron compounds, $BF_3$, $BCl_3$, tetrafluoroborate, and other halides, esters of boric acid (e.g., methyl borate, phenyl borate) and so on. A preferred boron compound includes boron hydrides, orthoboric acid, and other boric acids or salts thereof, among which a boric acid can preferably be employed. These co-catalysts may be employed singly or in combination.

The hydroxide includes $Mn(OH)_2$, $MnO(OH)$, $Fe(OH)_2$ and $Fe(OH)_3$, typically speaking. Examples of the metallic oxide include $Sm_2O_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$, and so forth. As examples of the double oxide or oxygen acid salt, there may be mentioned $MnAl_2O_4$, $MnTiO_3$, $LaMnO_3$, $K_2Mn_2O_5$, $CaO \cdot xMnO_2$(x=0.5, 1, 2, 3, 5), manganese salts [e.g., $Na_3MnO_4$, $Ba_3[MnO_4]_2$ and other manganates(V), $K_2MnO_4$, $Na_2MnO_4$, $BaMnO_4$, and other manganates(VI), $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, $Cd(MnO_4)_2$, and other permanganates].

As the organic acid salts, there may be exemplified as cobalt acetate, manganese acetate, cobalt propionate, manganese propionate, cobalt naphthenate, manganese naphthenate, cobalt stearate, manganese stearate, and other salts with a $C_{2-20}$ fatty acid, manganese thiocyanate, and corresponding salts of Ce, Ti, Zr, V, Cr, Mo, Fe, Ru, Ni, Pd, Cu and Zn. The inorganic acid salt includes, for instance, cobalt nitrate, iron nitrate, manganese nitrate, nickel nitrate, copper nitrate, and other nitrates, and sulfates, phosphates and carbonates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned, for instance, $SmCl_3$, $SmI_2$, $TiCl_2$, $ZrCl_2$, $ZrOCl_2$, $VCl_3$, $VOCl_2$, $MnCl_2$, $MnCl_3$, $FeCl_2$, $FeCl_3$, $RiuCl_3$, $CoCl_2$, $RhCl_2$, $RhCl_3$, $NiCl_2$, $PdCl_2$, $PtCl_2$, $CUCl$, $CuCl_2$, and other chlorides, or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, $CuBr$, $CuBr_2$), and other halides, $M^1MnCl_3$, $M^1{}_2MnCl_4$, $M^1{}_2MnCl_5$, $M^1{}_2MnCl_6$, wherein $M^1$ represents a monovalent metal, and other complex halides.

The ligand constituting the complex includes, for example, OH (hydroxo), methoxy, ethoxy, propoxy, butoxy and other alkoxy groups, acetyl, propionyl and other acyl groups, methoxycarbonyl (acetato), ethoxycarbonyl and other alkoxycarbonyl groups, acetylacetonato, cyclopentadienyl group, chlorine, bromine and other halogen atoms, CO, CN, oxygen atom, $H_2O$ (aquo), phosphine (e.g., triphenylphosphine and other triarylphosphine) and other phosphorus compounds, $NH_3$ (ammine), NO, $NO_2$ (nitro), $NO_3$ (nitrato), ethylenediamine, diethylenetriamine, pyridine, phenanthroline and other nitrogen-containing compounds. In the complexes or complex salts, the same or different ligands may be coordinated singly or in combination.

The ligand is practically, for example, OH, an alkoxy group, an acyl group, an alkoxycarbonyl group, acetylacetonato, a halogen atom, CO, CN, $H_2O$ (aquo), triphenylphosphine or other phosphorus compounds, or a nitrogen-containing compound inclusive of $NH_3$, $NO_2$ and $NO_3$.

The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu or Zn, titanylacetylacetonato complex $TiO(AA)_2$, zirconylacetylacetonato complex $ZrO(AA)_2$, vanadylacetylacetonato complex $VO(AA)_2$], cyano complexes [e.g., hexacyanomanganate(I), hexacyanoferrate(II)], carbonyl complexes or cyclopentadienyl complexes [e.g., tricarbonylcyclopentadienylmanganese(I), biscyclopentadienylmanganese(II), biscyclopentadienyliron (II), $Fe(CO)_5$, $Fe_2(CO)_9$, $Fe_3(CO)_{12}$], nitrosyl compounds [e.g., $Fe(NO)_4$, $Fe(CO)_2(NO)_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$].

The polyacid (isopolyacid or heteropolyacid) is practically at least one member selected from Group 5A elements or Group 6A elements of the Periodic Table of Elements, such as V (vanadic acid), Mo (molybdic acid) or W (tungstic acid), typically speaking. There is no particular limit as to the central atom, and it may be any of, for instance, Cu, Be, B, Al, Si, Ge, Sn, Ti, Th, N, P, As, Sb, V, Nb, Ta, Cr, Mo, W, S, Se, Te, Mn, I, Fe, Co, Ni, Rh, Os, Ir, Pt, or Cu. As illustrative examples of the heteropolyacid, there may be mentioned cobaltmolybdate, cobalttungstate, molybdenumtungstate, manganesemolybdate, manganesetungstate, manganesemolybdenumtungstate, vanadomolybdophosphate, manganesevanadiummolybdate, and manganesevanadomolybdophosphate. In the co-catalyst constituting the oxidation catalytic system of the present invention, a preferred polyacid is an isopolyacid, and the heteropolyacid of vanadiummolybdenum (phosphovanadomolybdate) or its salt is excluded.

These co-catalysts may be employed independently or in combination according to the species of the substrate. Depending on the species of the co-catalyst, any of the following characteristic functions, for example, can be exhibited.

1. In the constitutive transition metal compound of the co-catalyst, the valency of the element is not particularly restricted, and it may be about from two to six valencies. Use of a divalent transition metal compound (e.g., a divalent cobalt compound, a divalent manganese compound) as the co-catalyst enhances oxidation activity. By way of illustration, a catalytic system comprising the imide compound in combination with a divalent transition metal compound in lieu of a trivalent transition metal compound induces an oxidized product in a short time with high selectivity and yield. Further, when the divalent transition metal compound (e.g., a compound containing a Group 8 element of the Periodic Table of Elements such as divalent cobalt) is used as the co-catalyst, the substrate (e.g., an aromatic compound substituted with a methyl group) can be oxidized quantitatively to form a corresponding oxide (e.g., a carboxylic acid) even at a low temperature (e.g., 10 to 60° C.), in particular at room temperature (about 15 to 30° C.).

2. Use of a compound containing at least one element selected from Group 4A elements (e.g., Ti, Zr), Group 6A elements (e.g., Cr, Mo) and Group 7A elements (e.g., Mn) of the Periodic Table of Elements inhibits inactivation (deactivation) of the catalyst (in particular the imide compound) even in severe reaction conditions. Therefore, the process insures oxidation of the substrate with oxygen or air with commercial advantages.

3. The use of a compound containing the Group 4A element (e.g., Ti, Zr), Group 5A element (e.g., V), Group 6A element (e.g., Cr, Mo), Group 7A element (e.g., Mn) or Group 8 element (e.g., Fe, Co) of the Periodic Table of Elements as the co-catalyst results in remarkable enhancement of the oxidizing activity and provides effective oxidation of the substrate. By way of an example, a catalytic system comprising, as the co-catalyst, a compound containing the Group 5A element (e.g., V), Group 7A element (e.g., Mn) or Group 8 element (e.g., Co) of the Periodic Table of Elements has high activities. A catalytic system comprising, as the co-catalyst, a compound containing the Group 7A element (e.g., Mn) or Group 8 element (e.g., Fe) of the Periodic Table of Elements has high activities for the substrate (e.g., a cycloalkane) and provides a corresponding oxide (e.g., a ketone or dicarboxylic acid) with high selectivity. In particular, when a compound containing the Group 5A element (e.g., V) is used as the co-catalyst, plural positions or sites of the substrate [e.g., a bridgehead position or junction position of the polycyclic hydrocarbon (e.g., adamantane)] can be efficiently oxidized to give a product having plural introduced hydroxyl groups (e.g., an adamantanepolyol).

4. A combination use of the imide compound of the formula (1) with the co-catalyst containing the Group 1B element of the Periodic Table of Elements (e.g., Cu) as the oxidation catalytic system insures great improvement of the selectivity in the oxidation reaction, and inhibits deactivation of the imide compound. Therefore, this combination is advantageous for commercial production.

5. A use of the oxidation catalytic system comprising a combination of the imide compound of the formula (1), a compound containing the Group 7A element of the Periodic Table of Elements (e.g., a manganese compound), and a compound containing the Group 8 element of the Periodic Table of Elements (e.g., an iron compound) has further enhanced catalytic activities and provides effective and efficient production of an oxide with high transformation rate and selectivity. In this complex catalytic system, a ratio of the compound containing the Group 8 element of the Periodic Table of Elements (the second co-catalyst) is not particularly limited, and is, for instance, about 0.1 to 25 moles (e.g., about 0.1 to 20 moles), preferably about 0.2 to 15 moles, and more preferably about 0.5 to 10 moles relative to one mole of the compound containing the Group 7A element of the Periodic Table of Elements (the first co-catalyst).

The oxidation catalyst comprising the imide compound, or the oxidation catalytic system comprising the imide compound and the co-catalyst may be whichever of a homogeneous system or a heterogeneous system. The oxidation catalyst or oxidation catalytic system may be a solid catalyst comprising a catalytic component supported on a support or carrier, as well. As the support, use can be practically made of activated carbon, zeolite, silica, silica-alumina, bentonite, or other porous supports. In the solid catalyst, a supporting amount of the catalytic component may be such that a relative ratio of the imide compound of the formula (1) to 100 parts by weight of the support is about 0.1 to 50 parts by weight, preferably about 0.5 to 30 parts by weight and more preferably about 1 to 20 parts by weight. A ratio of the co-catalyst supported on the support is about 0.1 to 30 parts by weight, preferably about 0.5 to 25 parts by weight, and more preferably about 1 to 20 parts by weight, relative to 100 parts by weight of the support.

A relative ratio of the co-catalyst to the imide compound of the formula (1) may be selected from a range not interfering with the reaction rate and selectivity, and is, for example, about 0.001 to 10 moles, preferably about 0.005 to 5 moles, and more preferably about 0.01 to 3 moles relative to one mole of the imide compound. The co-catalyst may practically be employed in an amount of 0.01 to 5 moles (in particular 0.001 to 1 mole) relative to one mole of the imide compound.

Incidentally, the activity of the imide compound may sometimes deteriorate with an increasing ratio of the co-catalyst. Therefore, for retaining the high activities of the oxidation catalytic system, a preferred ratio of the co-catalyst, relative to one mole of the imide compound, is not less than an effective amount and not greater than 0.1 mole (e.g., about 0.001 to 0.1 mole, preferably about 0.005 to 0.08 mole, and more preferably about 0.01 to 0.07 mole).

A ratio of the imide compound of the formula (1) in the oxidation reaction (i.e., in the production of a ketone, an aldehyde or an alcohol) is selected from a broad range of about 0.001 to 1 mole (0.01 to 100 mole %), preferably about 0.001 to 0.5 mole (0.1 to 50 mole %), more preferably about 0.01 to 0.30 mole and practically about 0.01 to 0.25 mole, on 1 mole of the substrate, typically speaking.

A ratio of the co-catalyst (a co-oxidizing agent) used in such a reaction can be liberally selected from a range not interfering with the activity and selectivity, and is, for example, about 0.0001 mole (0.01 mole %) to 0.7 mole (70 mole %), preferably about 0.0001 to 0.5 mole, and more preferably about 0.001 to 0.3 mole relative to one mole of the substrate. The co-catalyst is practically used in a ratio of 0.0005 to 0.1 mole (e.g., about 0.005 to 0.1 mole) per one mole of the substrate.

When the polyacid (an isopolyacid or a heteropolyacid) or its salt is used as the co-catalyst, the ratio of it is, relative to 100 parts by weight of the substrate, about 0.1 to 25 parts by weight, preferably about 0.5 to 10 parts by weight, and more preferably about one to five parts by weight.

Substrate

The use of the oxidation catalyst comprising the imide compound, or the oxidation catalytic system comprising the imide compound and the co-catalyst insures effective oxidation of various substrates, and provides ketones, alcohols, aldehydes or carboxylic acids each corresponding to the substrates. A species of the substrate is not strictly limited, and saturated or unsaturated compounds in broad range can be employed. The substrate includes, for example, hydrocarbons (aliphatic hydrocarbons, alicyclic hydrocarbons, aromatic hydrocarbons), heterocyclic compounds, alcohols, ethers, esters, ketones, aldehydes and amines.

These substrates may have, according to the species of the substrate, any of various substrates. Examples of such substrates include halogen atoms (iodine, bromine, chlorine and fluorine atoms), alkyl groups (e.g., methyl, ethyl, propyl, isopropyl, butyl, isobutyl, sec-butyl, t-butyl, hexyl and other straight chain or branched chain alkyl groups each having about 1 to 6 carbon atoms, in particular lower alkyl groups each having about 1 to 4 carbon atoms), an oxo group, a hydroxyl group, alkoxy groups (e.g., methoxy, ethoxy, propoxy, isopropoxy, butoxy, isobutoxy, t-butoxy, hexyloxy and other alkoxy groups each having about 1 to 6 carbon atoms, in particular lower alkoxy groups each having about 1 to 4 carbon atoms), hydroxyalkyl groups (e.g., hydroxymethyl, 2-hydroxyethyl and other hydroxy-$C_{1-4}$ alkyl groups), a carboxyl group, alkoxycarbonyl groups (e.g., methoxycarbonyl, ethoxycarbonyl, propoxycarbonyl, isopropoxycarbonyl, butoxycarbonyl, isobutoxycarbonyl, t-butoxycarbonyl, hexyloxycarbonyl and other alkoxycarbonyl groups each having about 1 to 6 carbon atoms in the alkoxy moiety, in particular lower alkoxycarbonyl groups each having about 1 to 4 carbon atoms in the alkoxy moiety), acyl groups (e.g., formyl, acetyl, propionyl, butyryl, isobutyryl, valeryl, isovaleryl, pivaloyl, and other acyl groups each having about 1 to 6 carbon atoms), an amino group, a substituted amino group, a cyano group, a nitro group and the like.

As preferred substrates, there may be mentioned the following compounds that are useful for commercial applications.

(a) Cycloalkane

The cycloalkane includes, for instance, compounds each having a cycloalkane ring of 3 to 30 members, such as cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclohexadecane, cyclooctadecane, cyclononadecane, cycloicosane, cyclodocosane, cyclotetracosane, or cyclotriacontane.

As the cycloalkanes having a substituent, there may be mentioned, for example, cycloalkanes each having a hydroxyl group (e.g., cyclohexanol, cyclooctanol, cyclodecanol, cycloundecanol, cyclododecanol, cyclotetradecanol, cycloicosanol), cycloalkanes each having an oxo group (e.g., cyclopentanone, cyclohexanone, methylcyclohexanone, dimethylcyclohexanone, cyclohexadione, cyclopentanone, cyclooctanone, cyclooctadione, cyclononanone, cyclodecanone, cycloundecanone, cyclododecanone, cyclotetradecanone, cyclooctadecanone, cycloicosanone), cycloalkanes each having an alkyl group (e.g., methylcyclohexane, 1,2-dimethylcyclohexane, isopropylcyclohexane, methylcyclooctane) and so on.

A preferred cycloalkane includes compounds each having a ring of about 5 to 30 members, in particular a ring of about 6 to 25 members, among which compounds each having a ring of about 6 to 20 members (e.g., a 6- to 16-membered ring) are desirable, typically speaking.

Further, according to the process of the present invention, effective oxidation can be achieved for compounds each having a ring of 8 members or more (e.g., a ring of about 8 to 30 members), preferably a ring of about 8 to 25 members, in particular, a ring of about 8 to 20 members (e.g., a ring of 8 to 16 members) which are commercially useful.

Oxidation of such a cycloalkane with oxygen in the presence of the oxidation catalyst comprising the imide compound of the formula (1), or the catalytic system comprising the imide compound of the formula (1) and the co-catalyst mainly provides a corresponding dicarboxylic acid or cycloalkanone with a high transformation rate and selectivity even in air or oxygen atmosphere at ambient pressure (atmospheric pressure).

By way of illustration, when cyclohexane or its derivative (e.g., cyclohexanone or cyclohexanol) is oxidized, adipic acid can efficiently be formed with a high transformation rate and excellent selectivity.

As the substrate (an alicyclic $C_6$ compound) for the production of adipic acid, use can be made of cyclohexane, cyclohexanol or cyclohexanone. At least one member selected from cyclohexane, cyclohexanol or cyclohexanone may only be used as the substrate, and a combination of two members may also be employed. Incidentally, a single use of cyclohexane insures the formation of adipic acid with a high transformation rate and selectivity. The oxidation of cyclohexane in the presence of cyclohexanol or cyclohexanone, each of which is an oxide of cyclohexane, or oxidation of cyclohexanol or cyclohexanone insures further enhancement of the transformation rate and selectivity.

The oxidation of cyclohexane or its derivative according to the oxidation process is characterized in that a by-product scarcely forms and that most of the products are adipic acid not only in mild conditions but also at an accelerated reaction rate at a high reaction temperature and/or a high reaction pressure. Therefore, adipic acid can be separated and purified with great ease in a simple manner, and the process is significantly useful for the production of adipic acid used as a raw material of nylon 66, polyester, or a plasticizer.

The use of the oxidation catalyst or the oxidation catalytic system insures specific and remarkable increase of the reactivity with respect to oxygen, and provides oxidation with high efficiency to give a ketone (in particular, a monoketone) or a dicarboxylic acid in a high yield, even for a macrocyclic cycloalkane having 8 members or more, in particular 9 members or more (e.g., a 10- to 30-membered cycloalkane), which has little activity to oxidation. To be specific, a macrocyclic cycloalkane can be oxidized in mild conditions with a high transformation rate and selectivity to provide a ketone or a dicarboxylic acid (in particular, a macrocyclic monoketone or a long-chain dicarboxylic acid) according to the process of the invention. By way of example, oxidation of cyclooctane provides cyclooctanone or suberic acid. Oxidation of a cycloalkane having 9 members or more on contact with oxygen provides a corresponding cycloalkanone or a long-chain dicarboxylic acid. Such a monoketone may be a precursor of a dicarboxylic acid, and a raw material for the production of a lactam. Further, the monoketone is transformed into a corresponding dicarboxylic acid in progress of the reaction. Therefore, this process is remarkably useful for the production of a long-chain dicarboxylic acid having 8 or more carbon atoms, which is used as a raw material for polyester, polyamide or a plasticizer, or for the production of a monoketone compound that is a precursor of the long-chain dicarboxylic acid.

When the cycloalkane is used as the substrate, a practically effective co-catalyst comprises a compound containing at least a Group 7A element (e.g., Mn) of the Periodic Table of Elements. An effective co-catalyst may comprise a combination of a compound containing the Group 7A element (e.g., Mn) of the Periodic Table of Elements with a compound containing the Group 8 element (e.g., Fe) of the Periodic Table of Elements.

A use of a divalent transition metal compound (e.g., a divalent cobalt compound or a divalent manganese compound) insures production of a cycloalkanone (e.g., cyclooctanone), in particular, a dicarboxylic acid (e.g., suberic acid) from a corresponding cycloalkane (e.g., cyclooctane) with significantly improved selectivity and yield. Such a use also provides remarkable inhibition of by-production of a diketone.

(b) Cycloalkene

Examples of the cycloalkene include compounds each having a cycloalkene ring having 3 to 30 members, such as a cyclic olefin (e.g., cyclopropene, cyclobutene, cyclopentene, cyclohexene, 1-methyl-1-cyclohexene, isophorone, cycloheptene, cyclooctene, cyclononene, cyclodecene, cyclodecaene, cyclododecaene), a cycloalkadiene (e.g., cyclopentadiene, 1,3-cyclohexadiene, 1,4-cyclohexadiene and other cyclohexadienes, 1,3-cycloheptadiene and other cycloheptadienes, 1,5-cyclooctadiene and other cyclooctadienes, cyclodecadiene, cyclododecadiene), a cycloalkatriene (e.g., cyclooctatriene), a cycloalkatetraene (e.g., cyclooctatetraene), and so forth. A preferred cycloalkene includes compounds each having a 3- to 30-membered ring (e.g., a 3- to 20-membered ring), preferably a 3- to 16-membered ring, and specifically a 3- to 12-membered ring (e.g., a 5- to 10-membered ring).

As illustrative cycloalkenes having a substituent, there may be mentioned a cycloalkene having a $C_{1-4}$ alkyl group, a hydroxyl group, a hydroxyalkyl group, or a carboxyl group (e.g., cyclohexenecarboxylic acid, cyclohexenedicarboxylic acid, cyclohexadienecarboxylic acid, cyclohexadienedicarboxylic acid, cyclogeranic acid, cyclogeraniol, cyclocitral, cyclogeraniolene), and a cycloalkenone having an oxo group (e.g., cyclohexenone, cyclooctenone).

The imide compound has high oxidizing activities, and provides efficient oxidation of the cycloalkene with oxygen even in mild conditions by catalytically promoting the oxidation of the cycloalkene. Therefore, the use of the imide compound insures efficient oxidation of the cycloalkene to give a corresponding oxide of the cycloalkene (e.g., a ketone, an alcohol, an aldehyde or a carboxylic acid), in particular, a cycloalkenone or a cycloalkenol with high selectivity. Further, oxidation of the cycloalkene in the coexistence of the imide compound of the formula (1) and the co-catalyst provides further improvement of the transformation rate and/or selectivity.

(c) Polycyclic hydrocarbon having a methylidyne group as a constitutive element of the ring The polycyclic hydrocarbon includes bridged cyclic hydrocarbons (e.g., cross-linked hydrocarbons, terpenes) and condensed polycyclic hydrocarbons each having at least one methylidyne group (i.e., methine carbon-hydrogen bond —CH<). The ring having the methylidyne group is generally a non-aromatic ring, and it may be a bridged ring or a condensed ring each having an unsaturated double bond. A condensed polycyclic hydrocarbon that has been ortho-condensed or ortho and peri-condensed may have an aromatic ring condensed thereto as far as having a non-aromatic ring containing a methylidyne group. In such a polycyclic hydrocarbon, two or more methylidyne groups are practically present in the bridgehead positions and/or junction positions (fusing sites).

Some bridged cyclic hydrocarbons may form condensed polycyclic hydrocarbons in which adjacent rings bond each other in or at two methylidyne groups that are commonly possessed. In such a compound, it is possible to oxidize at least one methylidyne group in the bridgehead position and junction position and introduce a hydroxyl group into a tertiary carbon atom. A position of the hydroxyl group to be introduced may be selected according to the species of the substrate. The oxo group may practically be introduced into an adjacent position (a secondary carbon atom) to the bridgehead position and junction position.

As the cross-linked cyclic hydrocarbon among the bridged cyclic hydrocarbons, there may be mentioned, for example, bicyclic hydrocarbons (e.g., thujane, carane, pinane, bornane (camphane), bornylene, norbornene, norbornane, bicyclo[3.2.1]octane, bicyclo[4.3.2]undecane), tricyclic hydrocarbons (e.g., tricyclo[4.3.1.1$^{2,5}$]undecane, homobrendane (i.e., tricyclo[5.2.1.0$^{3,8}$]decane), adamantane, exotricyclo[5.2.1.0$^{2,6}$]decane, endotricyclo[5.2.1.0$^{2,6}$]decane, tricyclo[4.3.1.1$^{2,5}$]undecane, endotricyclo[5.2.2.0$^{2,6}$]undecane), tetracyclic hydrocarbons (e.g., tetracyclo[4.4.0.1$^{2,5}$.1$^{7,10}$]dodecane), and dicyclohexadiene, dicyclopentadiene and other dimers of dienes, hydrogenated products of these dimers (e.g., dicyclohexane, dicyclopentane, dicyclopentene, dicyclohexadiene, dicyclopentadiene) and their derivatives.

As the cross-linked cyclic hydrocarbons, use may be practically made of bicyclic through tetracyclic hydrocarbons each having about 7 to 16 constitutive carbon atoms of the rings (in particular, about 6 to 14 constitutive carbon atoms of the rings), inclusive of compounds each having carbon-hydrogen bonds in 2 or more bridgehead positions or junction sites. Among them, pinane, bornane, bornylene, norbornene, norbornane and other bicyclic hydrocarbons, tricyclo[4.3.1.1$^{2,5}$]undecane, homobrendane, adamantane and other tricyclic hydrocarbons may advantageously be employed. The cross-linked cyclic hydrocarbon in which a hydroxyl group can be introduced into a tertiary carbon atom in or at a bridgehead position includes, for instance, norbornene, tricyclo[4.3.1.1$^{2,5}$]undecane, homobrendane, adamantane and derivatives of these compounds.

Examples of the cross-linked cyclic hydrocarbon, in which a hydroxyl group can be introduced into a tertiary carbon atom in or at a junction site, include exotricyclo[5.2.1.0$^{2,6}$]decane, endotricyclo[5.2.1.0$^{2,6}$]-decane, tricyclo[4.3.1.1$^{2,5}$]undecane, endotricyclo[5.2.2.0$^{2,6}$]undecane, tetracyclo[4.4.0.1$^{2,5}$.1$^{7,10}$ ]dodecane, and the like.

As the terpenes, there may be mentioned, for instance, monocyclic monoterpenes (e.g., limonene, terpinolene, terpinene, phellandrene, menthene), bicyclic monoterpenes (e.g., carone, pinene, pinane, camphor, camphene, bornene, thujone, phencone), monocyclic sesquiterpenes (e.g., bisabolene, zingiberene), bicyclic sesquiterpenes (e.g., cadinene, santalene, selinene, santonin, caryophyllene), tricyclic sesquiterpenes (e.g., copaene, santalene, longifolene), diterpenes (e.g., vitamin A), triterpenes (e.g., ambrein, amyrin, lupeol), tetraterpenes (e.g., carotene, lutein and other carotenoids), polyterpenes and derivatives of these compounds.

The condensed polycyclic hydrocarbon includes various compounds formed by hydrogenation of condensed polycyclic aromatic hydrocarbons each condensed with a 5- to 8-membered ring, typically speaking. Such a compound includes, for instance, decalin, perhydroacenaphthylene, perhydroanthracene, perhydrophenanthrene, perhydrophenalene, hexahydroindane and so on. In the condensed polycyclic hydrocarbon, a five- or six-membered ring may practically be condensed, and the methylidyne group in or at a junction site may usually be oxidized.

As examples of the derivative of the cross-linked cyclic hydrocarbon among the polycyclic hydrocarbons each having a substituent, there may be mentioned derivatives each having a halogen atom (e.g., 2-chloronorbornane, 1-chloroadamantane, 1,3-dichloroadamantane), derivatives each having an alkyl group (e.g., 2,2-dimethylnorbornane, 2,7,7-trimethyl-2-norbornene, 1-methyladamantane, 1-ethyladamantane, 1-n-propyladamantane, 1-isopropyladamantane, 1-n-butyladamantane, 1-s-butyladamantane, 1-t-butyladamantane, 1-pentyladamantane, 1-hexyladamantane, 1-cyclohexyladamantane, 1,3-dimethyladamantane, 1-methyl-3-ethyladamantane, 1,3-dicyclohexyladamantane, 1,3,5-trimethyladamantane, 1-ethyl-3,5-dimethyladamantane, hemiadamantane, and other compounds each having an alkyl group containing about 1 to 6 carbon atoms), derivatives each having a hydroxyl group (e.g., camphenilol, borneol, isoborneol, 1-adamantanol, 1,3-adamantanediol, 1,3,5-adamantanetriol, 1-methyl-3-adamantanol, 1-methyl-3,5-adamantanediol, 1-ethyl-3-adamantanol, 1-ethyl-3,5-adamantanediol, 1,3-dimethyl-5-adamantanol, 1-methyl-3-ethyl-5-adamantanol, 1-propyl-3-adamantanol, 1-propyl-3,5-adamantanediol), derivatives each having an alkoxy group (e.g., 1-methoxyadamantane, 1,3-dimethoxyadamantane, 1-ethoxyadamantane, 1,3-diethoxyadamantane), derivatives each having an oxo group (e.g., camphorquinone, camphenilone, 2-adamantanone, methyladamantanone, dimethyladamantanone), derivatives each having an acyl group (e.g., formylnorbornene, formyladamantane), derivatives each having a carboxyl group (e.g., camphanic acid, camphenylic acid), derivatives each having an alkyloxycarbonyl group (e.g., methoxycarbonylcamphane, ethoxycarbonylcamphenyl), derivatives each having an amino group (e.g., bornylamine), derivatives each having a vinyl group (e.g., vinylnorbornene), and so forth.

As the cyclic terpene derivatives, there may be mentioned, for example, cyclic terpene alcohols (e.g., menthol, carbomenthol, terpineol, carveol), cyclic terpene aldehydes (e.g., carbomenthone, phellandral, perillaldehyde), cyclic terpene ketones (e.g., ionone, irone, menthone, carbomenthone, thujone), cyclic terpene oxides (e.g., cineol, pinol, ascaridol), cyclic terpene carboxylic acids (e.g., camphenic acid, camphoric acid, abietic acid, neoabietic acid, levopimaric acid, dextropimaric acid), and so on.

The derivatives of the condensed polycyclic hydrocarbon includes derivatives each having an alkyl group (e.g., methyldecalin, ethyldecalin, n-propyldecalin, isopropyldecalin, n-butyldecalin, s-butyldecalin, t-butyldecalin, cyclohexyldecalin, dimethyldecalin, methylethyldecalin, trimethyldecalin, ethyldimethyldecalin, tetramethyldecalin, and hexahydroindanes corresponding to these compounds), derivatives each having a hydroxyl group (e.g., decalol), derivatives each having an oxo group (e.g., decalone), derivatives each having a carboxylic acid (e.g., decalincarboxylic acid), and derivatives each having an amino group (e.g., decalylamine), typically speaking.

The use of the oxidation catalyst comprising the imide compound, or the oxidation catalytic system comprising the imide compound and the co-catalyst insures efficient oxidation, with oxygen, of the polycyclic hydrocarbon containing a methylidyne group as a constitutive unit of the ring, and provides an oxide (a ketone, an alcohol, an aldehyde, a carboxylic acid) of the polycyclic hydrocarbon, in particular a ketone or an alcohol thereof with high selectivity. Therefore, the process of the present invention, in which the polycyclic hydrocarbon (e.g., a polycyclic hydrocarbon having 2 to 4 rings containing methylidyne groups in plurality of bridgehead positions or junction sites) is allowed to contact oxygen, provides a hydroxyl group-containing polycyclic hydrocarbon having a hydroxyl group being introduced into the bridgehead position or junction site with high selectivity and an excellent yield.

To be specific, the use of a catalytic system comprising the imide compound and the divalent transition metal compound, or a catalytic system comprising the imide compound and a compound containing an element selected from Group 4A elements (e.g., Ti, Zr), Group 5A elements (e.g., V), Group 6A elements (e.g., Cr, Mo), Group 7A elements (e.g., Mn) or Group 8 elements (e.g., Co) of the Periodic Table of Elements insures improvement of the transformation rate of the polycyclic hydrocarbon, and it provides a hydroxyl group-containing polycyclic hydrocarbon with high selectivity and an enhanced yield.

When the adamantane component is used as the substrate, an adamantanepolyol may be formed by introducing hydroxyl groups into plural bridgehead positions of adamantane directly or indirectly, according to the process of the invention. Such an adamantanepolyol having hydroxyl groups introduced into plural bridgehead positions may be prepared by any of the following technologies: (1) a process of contacting the adamantane component selected from adamantane or its derivative with oxygen in the presence of the oxidation catalytic system comprising the imide compound and the co-catalyst, or (2) a process of contacting the adamantane component containing at least one component selected from an adamantanemonool, an adamantanediol and adamantanetriol in the presence of the oxidation catalyst comprising the imide compound, or in the presence of the oxidation catalytic system comprising the imide compound and the co-catalyst to give a higher adamantanepolyol which has been further hydroxylated.

According to the process (1), a proper selection and combination of the imide compound and the co-catalyst strongly inhibits the formation of a ketone that becomes significant disturbance to isolation and purification of the adamantanepolyol, and provides an adamantanepolyol in a remarkably improved yield. By way of example, when the adamantane component is oxidized in the presence of a catalytic system comprising a combination of the imide compound and a divalent transition metal compound (e.g., a divalent cobalt compound) as the co-catalyst, a polyol such as an adamantanediol can be obtained with high selectivity and an enhanced yield even in mild or moderate conditions. In such preparation, a ketone is scarcely by-produced. In particular, even when the reaction is conducted at a higher temperature or for a prolonged reaction time, the polyol such as an adamantanediol can be produced in a larger amount than an adamantanemonool with scarce by-production of a ketone.

Further, the use of a compound, as the co-catalyst, containing an element selected from Group 4A elements, Group 5A elements, Group 6A elements, Group 7A elements and Group 8 elements of the Periodic Table of Elements insures production of a polyol such as an adamantanediol, in particular an adamantanetriol or adamantanetetraol from the adamantane component with improved selectivity and an excellent yield. Among them, a compound containing the Group 5A element (e.g., V) can advantageously be used as the co-catalyst.

According to the process (2), an adamantanepolyol, in which more hydroxyl groups are introduced, can be prepared with effectiveness and a high yield. To be specific, a further hydroxylated adamantanepolyol can be obtained by oxidizing the adamantane component with oxygen in the presence of an alcohol of adamantane (e.g., with the use of an alcohol-form of adamantane alone, or the adamantane component containing an alcohol-form of adamantane and adamantane itself). As an illustrative example, oxidation of the adamantane component comprising an adamantanemonool and no other, or the adamantane component comprising an adamantanemonool and adamantane provides an adamantanepolyol in which hydroxyl groups have been introduced into two or more bridgehead positions (e.g., an adamantanediol, an adamantanetriol, an adamantanetetraol). Oxidation of the adamantane component comprising an adamantanediol and no other, or the adamantane component comprising an adamantanediol and adamantane provides an adamantanepolyol, in which hydroxyl groups have been introduced into three or more bridgehead positions (e.g., an adamantanetriol, an adamantanetetraol). Oxidation of the adamantane component comprising an adamantanetriol and no other, or an adamantanetriol and adamantane provides an adamantanetetraol. Accordingly, in the production of an adamantanepolyol, it is desirable to use the adamantane component containing at least one component selected from an adamantanemonool, an adamantanediol or an adamantanetriol for the formation of an adamantanepolyol having more hydroxyl groups introduced therein.

When the adamantanepolyol is prepared according to the process (2), the adamantane component may only be subjected to the reaction in the coexistence of at least an alcohol of adamantane. The ratio of the adamantanemonool, adamantanediol or adamantanetriol is not strictly limited, and is about 5 mole % or more (e.g., about 10 to 100 mole %), preferably about 20 to 100 mole % and more preferably about 30 to 100 mole %, based on the total amount of the adamantane component.

Also in the process (2), an effective co-catalyst includes the divalent transition metal compounds (e.g., a divalent cobalt compound) and compounds each containing an element selected from Group 4A elements, Group 5A elements, Group 6A elements, Group 7A elements and Group 8 elements of the Periodic Table of Elements.

(d) Aromatic compound having a methyl group or methylene group in an adjacent position of an aromatic ring The aromatic compound may only be an aromatic compound having at least one methyl group or methylene group being substituted on the aromatic ring. The aromatic ring may be whichever of an aromatic hydrocarbon ring or an aromatic heterocyclic ring. When the aromatic compound is a ring-assembled compound in which aromatic rings bond each other, such as biphenyl, terphenyl, binaphthalene or bipyridine, at least one aromatic ring may be substituted with a methyl group or methylene group. The methyl group or methylene group in the aromatic heterocyclic ring may be bonded to the heterocyclic ring or to an aromatic hydrocarbon ring of a condensed heterocycle. A preferred compound includes a compound having a methyl group or methylene group in the benzyl position.

As examples of the aromatic hydrocarbon, there may be mentioned a benzene ring, condensed cyclic hydrocarbon rings (e.g., naphthalene, anthracene, phenanthrene, triphenylene, pyrene, chrysene, naphthacene, benzanthracene, and other condensed rings as produced by ortho-condensation or ortho and peri-condensation of 2 to 8 benzene rings).

Examples of the aromatic heterocyclic ring include heterocyclic rings each having an oxygen atom as a heteroatom (e.g., furan, oxazole, isooxazole and other 5-membered rings, pyran and other 6-membered rings, benzofuran, isobenzofuran, dibenzofuran, xanthone, xanthene, chroman, isochroman, chromene and other condensed rings), heterocyclic rings each containing a sulfur atom as a hetero-atom (e.g., thiophene, thiazole, isothiazole, thiadiazole, benzothiophene), heterocyclic rings each containing a nitrogen atom as a hetero-atom (e.g., pyrrole, pyrazole, imidazole, triazole and other 5-membered rings, pyridine, pyridazine, pyrimidine, pyrazine and other 6-membered rings, indole, indolene, isoindole, indazole, indoline, isoindoline, quinoline, isoquinoline, quinolinequinoline, quinoxaline, quinazoline, phthalazine, purine, carbazole, acridine, naphthoquinoline, phenanthrodine, phenanthroline, naphthyridine, benzoquinoline, phenoxazine, phthalocyanine, anthracyanine and other condensed rings), and the like.

The aromatic compounds which are useful for commercial applications may practically have an aromatic hydrocarbon ring, a 6-membered heterocyclic ring or a condensed heterocyclic ring. Among them, compounds each having an aromatic hydrocarbon ring containing 6 to 14 carbon atoms, in particular an aromatic hydrocarbon ring with 6 to 10 carbon atoms (specifically, a benzene ring or a naphthalene ring) are desirable.

The process of the invention insures efficient oxidation of the methyl group or methylene group of the aromatic compound. Therefore, the number of a substituted methyl group(s) or methylene group(s) is not particularly restricted, and is selected from a broad range (e.g., about 1 to 10, and preferably about 1 to 8) depending on the species or size of the aromatic ring.

(d1) Aromatic compound substituted with a methyl group

The aromatic compound substituted with a methyl group includes, for instance, aromatic hydrocarbons each substituted with about one to six methyl groups [e.g., toluene, o-, m-, or p-xylene, 1,2,3-trimethylbenzene, 1,2,4-trimethylbenzene, 1,3,5-trimethylbenzene (mesitylene), 1,2,3,4-tetramethylbenzene, 1,2,3,5-tetramethylbenzene, 1,2,4,5-tetramethylbenzene (durene), 1,2,3,4,5,6-hexamethylbenzene, 1-methylnaphthalene, 2-methylnaphthalene, 1,5-dimethylnaphthalene, 2,5-dimethylnaphthalene, methylanthracene, dimethylanthracene, trimethylanthracene, 4,4'-dimethylbiphenyl], heterocyclic compounds each substituted with about one to six methyl groups [e.g., 2-methylfuran, 3-methylfuran, 2-methylpyran, 3-methylpyran, 4-methylpyran, 3,4-dimethylpyran, 4-methylchromene, 6-methylchroman, 2-methylpyridine, 3-methylpyridine, 4-methylpyridine, and other picolines, 2,3-dimethylpyridine, 2,4-dimethylpyridine, 2,5-dimethylpyridine, 3,5-dimethylpyridine and other lutidines, 2,3,4-trimethylpyridine, 2,3,5-trimethylpyridine, 2,3,6-trimethylpyridine, 2,4,6-trimethylpyridine, and other collidines, 4-methylindole, 5-methylindole, 7-methylindole, methylquinoline], and so on.

A preferred aromatic compound may practically have 1 to 4 methyl groups (e.g., one or two methyl groups) substituted in the molecule. Among such compounds, $C_{6-10}$ aromatic hydrocarbons and heterocyclic compounds containing a 5- or 6-membered heterocycle each having about one to four methyl groups are practically useful for commercial production of carboxylic acids. In particular, benzene derivatives each having a methyl group are advantageously employed.

(d2) Compound having a methylene group in an adjacent position to the aromatic ring The compound having a methylene group in an adjacent position to the aromatic ring includes aromatic compounds each having an alkyl group or a substituted alkyl group containing two or more carbon atoms, and aromatic compounds each having a cyclic methylene group.

As the aromatic compounds each having an alkyl group or a substituted alkyl group, there may be mentioned aromatic hydrocarbons each having an alkyl group [e.g., ethylbenzene, propylbenzene, cumene, butylbenzene, isobutylbenzene, 1,4-diethylbenzene, 1-ethyl-4-pentylbenzene and other aromatic hydrocarbons each having a $C_{2-6}$ alkyl group, dibenzyl, diphenylmethane, triphenylmethane, 1-benzylnaphthalene, and other aromatic hydrocarbons each having a substituted alkyl group], and heterocyclic compounds each having an alkyl group (e.g., ethylpyridine, isopropylpyridine, butylpyridine), typically speaking.

Examples of the aromatic compound having a cyclic methylene group include condensed polycyclic aromatic hydrocarbons each having a condensed 5- to 8-membered ring [e.g. dihydronaphthalene, indene, indane, tetralin, fluorene, phenalene, α-tetralone, β-tetralone, indanone] and the like.

The aromatic compound (d) may have a methylene group with a methyl group in an adjacent position to the aromatic ring, as well. As examples of such a compound, there may be mentioned alkyl-substituted hydrocarbons each having at least one methyl group and at least one $C_{2-10}$ alkyl group [e.g., 1-methyl-2-ethylbenzene, 1-methyl-3-ethylbenzene, 1-methyl-4-ethylbenzene, 1-methyl-3-isopropylbenzene, 1-methyl-4-isopropylbenzene (cymene), 1-methyl-4-propylbenzene, 1-methyl-4-butylbenzene, 1-methyl-4-t-butylbenzene, 1,2-dimethyl-3-ethylbenzene, 1,2-dimethyl-4-ethylbenzene, 1,3-dimethyl-5-ethylbenzene, 1,3-dimethyl-4-ethylbenzene, 1,3-dimethyl-2-ethylbenzene, 1,4-dimethyl-2-ethylbenzene, 1-methyl-2-ethylnaphthalene, and other alkyl-substituted hydrocarbons each having a methyl group and a $C_{2-6}$ alkyl group], alkyl-substituted heterocyclic compounds [e.g., 2-ethyl-4-methylpyridine, 3-ethyl-4-methylpyridine, 4-ethyl-2-methylpyridine], hydrocarbons each having at least one methyl group and a cyclic methylene group (e.g., 3-methylindene), and so on.

These aromatic compounds may have other substituents besides the methyl group or methylene group, as well. Such aromatic compounds include carboxyl group-substituted hydrocarbons [e.g., 4-methylbenzoic acid, 1,2-dimethylbenzene-4-carboxylic acid], halogen-containing hydrocarbons [e.g., 4-chloro-1-methylbenzene, 3,4,5,6-tetrachloro-1,2-dimethylbenzene, 3,4,5,6-tetrabromo-1,2-dimethylbenzene], hydroxyl group-containing hydrocarbons (e.g., cresols such as o-, m- or p-cresol, 2,3-xylenol, thymol), aromatic hydrocarbons each having a protected hydroxyl group [e.g., alkoxy group-containing hydrocarbons (e.g., 2-methoxy-1-methylbenzene, 3-methoxy-1-methylbenzene, 4-methoxy-1-methylbenzene, 4-ethoxy-1-methylbenzene, 4-isopropoxy-1-methylbenzene), acyloxy group-substituted hydrocarbons (e.g., 2-acetyloxy-1-methylbenzene, 3-acetyloxy-1-methylbenzene, 4-acetyloxy-1-methylbenzene, 4-propionyloxy-1-methylbenzene, 4-butyryloxy-1-methylbenzene)], amino group-containing hydrocarbons each of which may have a substituent [e.g., 4-amino-1-methylbenzene, 4-dimethylamino-1-methylbenzene], and other aromatic hydrocarbons, halogen-containing pyridine derivatives (e.g., 2-chloro-4-methylpyridine), and other heterocyclic compounds.

Oxidation of such an aromatic compound on contact with oxygen in the presence of the oxidation catalyst comprising the imide compound, or the oxidation catalytic system comprising the imide compound and the co-catalyst insures oxidation of the methyl group or the adjacent methylene group to the aromatic ring with greatly high efficiency. Thus, an aldehyde, in particular, a carboxyl group-containing aromatic compound can be obtained from the aromatic compound having a methyl group, and a ketone can be prepared from the methylene group-containing aromatic compound with high selectively and an excellent yield. In particular, such an oxidation process insures smooth progress of the reaction in a short period, and provides a carboxyl group-containing aromatic compound or a ketone with high selectivity in a high yield, even in mild conditions. Further, when an aromatic compound having plural methyl groups is oxidized, the process provides a carboxylic acid having a remained methyl group according to the progress of the reaction by controlling the reaction conditions such as a reaction time. According to the process, it is easy to form a polycarboxylic acid having two or more carboxyl groups by further proceeding the reaction. Therefore, the process of the invention is useful for the production of a carboxyl group-containing aromatic compound or ketone by contacting an aromatic compound having at least one methyl group or methylene group with oxygen. A preferred embodiment of the process of the invention includes a process of contacting a benzene derivative having a methyl group (e.g., toluene, xylene) with oxygen to produce a benzene derivative having a carboxyl group, which is useful for commercial applications (e.g., benzoic acid, phthalic acid, isophthalic acid, terephthalic acid), and a process of contacting a $C_{2-6}$ alkyl group-substituted aromatic hydrocarbon (e.g. ethylbenzene) with oxygen to give a carbonyl group-containing benzene derivative (e.g., acetophenone), which is a commercially useful compound.

The use of the divalent transition metal compound (e.g., a divalent cobalt compound) as the co-catalyst insures enhanced selectivity and yield of the polycarboxylic acid or ketone, even in such mild conditions as a low temperature (e.g., about 10 to 60° C.), in particular room temperature (about 15 to 30° C.). By way of illustration, oxidation of p-xylene provides terephthalic acid with high selectivity and in a high yield, under mild or moderate conditions, in a reaction time half as short as that of a conventional process. Incidentally, oxidation of o-xylene with air or oxygen also provides phthalic anhydride, if conducted in the presence of the catalytic system comprising the divalent transition metal compound in combination with the imide compound.

Accordingly, the process of the invention is effective for oxidation of the aromatic compound in mild conditions with high transformation rate and selectivity to give a carboxyl group-containing aromatic compound such as a monocarboxylic acid or polycarboxylic acid, or a ketone. In especial, the process is extremely useful for the production of an aromatic monocarboxylic acid inclusive of benzoic acid, or an aromatic polycarboxylic acid (in particular, an aromatic dicarboxylic acid) which is used as a raw material for the production of polyester or polyamide.

(e) Conjugate compound

The conjugate compound includes, for instance, a conjugate diene, an α,β-unsaturated nitrile or a compound shown by the following formula (2) (i.e., an α,β-unsaturated carboxylic acid or its derivative),

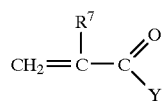

(2)

wherein $R^7$ represents a hydrogen atom or a methyl group; Y denotes —$OR^8$ or —$NR^9R^{10}$, where $R^8$ represents a hydrogen atom, an alkyl group, an aryl group, a cycloalkyl group, a hydroxyalkyl group, a glycidyl group or a dialkylamino-alkyl group, and where $R^9$ and $R^{10}$ respectively represent a hydrogen atom, an alkyl group or a hydroxyalkyl group.

As the conjugate dienes, there may be exemplified compounds each having a conjugate double bond such as butadiene (1,3-butadiene) and isoprene (2-methyl-1,3-butadiene), compounds each having a double bond and a triple bond (e.g., vinylacetylene, divinylacetylene) and derivatives of these compounds. Examples of the derivatives of the conjugate diene include 2-chlorobutadiene, 2,3-dichlorobutadiene, and other compounds each having a halogen atom (iodine, bromine, chlorine, or fluorine atom), 2-ethylbutadiene, 2,3-dimethylbutadiene, and other compounds each having an alkyl group (e.g., methyl, ethyl, propyl, isopropyl, butyl, isobutyl, sec-butyl, t-butyl, and other lower alkyl groups each having about one to four carbon atoms), butadiene-1-carboxylic acid and other compounds each having a carboxyl group. A preferred conjugate diene includes butadiene and isoprene.

Oxidation of the conjugate diene with oxygen provides an alkenediol. The substituted positions of hydroxyl groups of the produced alkenediol are not strictly limited as far as it being a diol corresponding to the conjugate diene. By way of example, a butenediol formed by oxidation of butadiene may be any of the 2-butene-1,4-diol or 1-butene-3,4-diol, and it may be either a cis-form or trans-form.

The α,β-unsaturated nitrile includes (meth) acrylonitrile, typically speaking.

The conjugate compound of the formula (2) corresponds to an α,β-unsaturated carboxylic acid or its derivative.

As the alkyl group in substituent $R^8$ in the formula (2), there may be mentioned, for example, methyl, ethyl, propyl, isopropyl, butyl, isobutyl, sec-butyl, t-butyl, pentyl, hexyl, heptyl, 2-ethylhexyl, octyl, decyl, tetradecyl, and other straight chain or branched chain alkyl groups each having about 1 to 20 carbon atoms. A preferred alkyl group includes alkyl groups each having about 1 to 15 carbon atoms, among which alkyl groups each having about 1 to 12 carbon atoms (e.g., about 1 to 10 carbon atoms) are desirable. The aryl group includes a phenyl group and a naphthyl group, typically speaking. Examples of the cycloalkyl group include cyclopentyl, cyclohexyl, cyclooctyl, and other cycloalkyl groups each containing a 5- to 10-membered ring.

The hydroxyalkyl group includes, for instance, 2-hydroxylethyl, 2-hydroxypropyl, 4-hydroxybutyl, hydroxypentyl and other hydroxyalkyl groups each having about 2 to 10 carbon atoms. A preferable hydroxyalkyl group includes hydroxyalkyl groups each having about 2 to 4 carbon atoms. Among them, hydroxyalkyl groups each having about 2 or 3 carbon atoms are advantageously used.

As the dialkylamino-alkyl group, there may be mentioned, for example, dimethylaminoethyl group, diethylaminoethyl group, dibutylaminoethyl group, and other di-$C_{1-4}$ alkylamino-$C_{2-3}$ alkyl groups.

The substituent $R^8$ may practically be a hydrogen atom, an alkyl group having 1 to 10 carbon atoms, a hydroxyalkyl group having two or three carbon atoms, or a glycidyl group.

Examples of the compound having such a substituent include (meth)acrylic acid; methyl (meth)acrylate, ethyl (meth)acrylate, isopropyl (meth)acrylate, n-butyl (meth)acrylate, isobutyl (meth)acrylate, hexyl (meth)acrylate, 2-ethylhexyl (meth)acrylate, lauryl (meth)acrylate, and other alkyl (meth)acrylates; 2-hydroxyethyl (meth)acrylate, 2-hydroxypropyl (meth)acrylate, and other hydroxyalkyl (meth)acrylates; glycidyl (meth)acrylate; dimethylaminoethyl (meth)acrylate, diethylaminoethyl (meth)acrylate, and the like.

In the substituted amino group —$NR^9R^{10}$ shown by "Y," the alkyl group of $R^9$ and $R^{10}$ includes methyl, ethyl, propyl, isopropyl, butyl, isobutyl, sec-butyl, t-butyl, pentyl and other alkyl groups each having about 1 to 10 carbon atoms, for example. An illustrative alkyl group includes alkyl groups each having about 1 to 6 carbon atoms, in particular, alkyl groups each having about 1 to 4 carbon atoms. Examples of the hydroxyalkyl group include hydroxy-$C_{1-10}$ alkyl groups, among which hydroxylmethyl and hydroxyethyl groups are preferable.

The substituents $R^9$ and $R^{10}$ may be the same or different from each other, and are practically any of a hydrogen atom, an alkyl group having about 1 to 4 carbon atoms, or a hydroxyalkyl group having 1 or 2 carbon atoms.

As the compounds having such a substituent, there may be mentioned, for instance, (meth)acrylamide, N-methyl(meth) acrylamide, N-methylol(meth)acrylamide, and other (meth) acrylamide derivatives.

Oxidation of the α,β-unsaturated nitrile, α,β-unsaturated carboxylic acid or its derivative on contact with oxygen insures selective oxidation of the α,β-unsaturated bond to give a compound shown by the following formula (3a) or (3b) with a high transformation rate and selectivity,

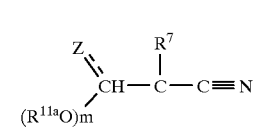

(3a)

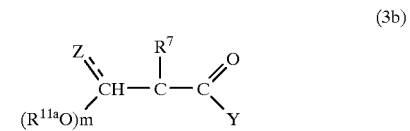

(3b)

wherein Z represents an oxygen atom or —OR $R^{11a}$ and $R^{11b}$ independently represent a hydrogen atom, an alkyl group or an acyl group, and m denotes 0 or 1, where the bond between the carbon atom "C" and "Z" denotes a single bond or a double bond; $R^7$ and Y have the same meanings as defined above; provided that Z is an oxygen atom, m is zero and the bond between the carbon atom C and the oxygen atom Z is a double bond, and provided that Z is —$OR^{11b}$, m is one and the bond between the carbon atom C and the substituent Z is a single bond.

The alkyl group of the substituents $R^{11a}$ and $R^{11b}$ in the compound of the formula (3a) or (3b) includes methyl, ethyl, propyl, isopropyl, butyl, isobutyl, sec-butyl, t-butyl and other $C_{1-6}$ alkyl groups, and the acyl group includes acetyl, propionyl and other $C_{2-6}$ acyl groups, typically peaking. These alkyl groups and acyl groups may sometimes form by a reaction with a solvent.

In this oxidation reaction, it is supposed that a diol (i.e., a compound where Z is —$OR^{11b}$, and both $R^{11a}$ and $R^{11b}$ are a hydrogen atom) mainly forms, and an aldehyde or its derivative (a compound where Z is an oxygen atom) may occasionally form by dehydration. The use of a protonic solvent (e.g., acetic acid, propionic acid or other organic acids, methanol, ethanol, n-propanol, isopropanol, n-butanol, t-butanol, or other alcohols) as a reaction solvent may sometimes provide a diol derivative inclusive of an acetal or acyloxy compound (a compound where Y is —OR$^{11b}$, and at least either R$^{11a}$ or R$^{11b}$ is an alkyl group or an acyl group). The aldehyde or its derivative, or a diol derivative inclusive of an acetal is an equivalent compound to the diol. For instance, oxidation of acrylonitrile with the use of an alcohol (e.g., methanol) as the reaction solvent sometimes provides a 1,1-dialkoxypropionitrile (e.g., 1,1-dimethoxypropionitrile). Further, a methyl 1,1-dialkoxypropionate (e.g., methyl 1,1-dimethoxypropionate) occasionally forms when methyl acrylate is oxidized in an alcohol (e.g., methanol) solvent.

As described above, the process of the present invention is useful for the production of an oxide by oxidation with air or oxygen of a corresponding conjugate compound, such as production of an alkenediol from a corresponding conjugate diene (e.g., butenediol from butadiene, which butenediol is employed as a raw material for the production of polyamide or other synthetic resins, maleic anhydride, a plasticizer, or butanediol). The process is also useful for the production of the compounds of the formulae (3a) and (3b) from the α,β-unsaturated nitrile, α,β-unsaturated carboxylic acid or its derivative.

(f) Other substrates

As the other substrates, there may be exemplified with a heterocyclic compound having a methylene group (f1), a chain hydrocarbon having a methine carbon atom (a methylidyne group) (f2), a compound having a methylene group in an adjacent position to an unsaturated bond (f3), and a compound having a methylene group in an adjacent position to a carbonyl group (f4).

(f1) Heterocyclic compound having a methylene group

The heterocyclic compound having a methylene group includes a 5- or 6-membered cyclic compound having a hetero-atom selected from a nitrogen atom, an oxygen atom or a sulfur atom, or a condensed heterocyclic compound in which a 5- or 6-membered ring having a hetero-atom is condensed to an aromatic ring. An example of such compound includes dihydrofuran, tetrahydrofuran, pyran, dihydropyran, tetrahydropyran, piperidine, piperazine, pyrrolidine, xanthene, and the like.

(f2) Chain hydrocarbon having a methine carbon atom (a methylidyne group)

As examples of the chain hydrocarbon having a methine carbon atom, there may be mentioned chain hydrocarbons each having a tertiary carbon atom, such as isobutane, isopentane, isohexane, 3-methylpentane, 2,3-dimethylbutane, 2-methylhexane, 3-methylhexane, 2,3-dimethylpentane, 2,4-dimethylpentane, 2,3,4-trimethylpentane, 3-ethylpentane, 2,3-dimethylhexane, 2,4-dimethylhexane, 3,4-dimethylhexane, 2,5-dimethylhexane, 2-propylhexane, 2-methylheptane, 4-methylheptane, 2-ethylheptane, 3-ethylheptane, 2,6-dimethylheptane, 2-methyloctane, 3-methyloctane, 2,7-dimethyloctane, 2-methylnonane, and other aliphatic hydrocarbons each having about 4 to 10 carbon atoms.

(f3) Compound having a methylene group in an adjacent position to an unsaturated bond The compound (f3) includes, for instance, chain unsaturated hydrocarbons each having about 3 to 12 carbon atoms as well as having a double bond and/or a triple bond, such as propylene, 1-butene, 2-butene, butadiene, 1-pentene, 2-pentene, isoprene, 1-hexene, 2-hexene, 1,5-hexadiene, 2,3-dimethyl-2-butene, 3-hexene, 1-heptene, 2-heptene, 1,6-heptadiene, 1-octene, 2-octene, 3-octene, 1,7-octadiene, 2,6-octadiene, 2-methyl-2-butene, 1-nonene, 2-nonene, decene (decaene), decadiene, dodecene, dodecadiene, dodecatriene, undecene, undecadiene, undecatriene, and so forth.

(f4) Compound having a methylene group in an adjacent position to a carbonyl group Examples of the compound having an (active) methylene group in an adjacent position to a carbonyl group include aldehydes, ketones, carboxylic acids or their derivatives.

The aldehyde includes, for instance, aliphatic aldehydes (e.g., acetaldehyde, propionaldehyde, butyraldehyde, isobutyraldehyde, pentylaldehyde, hexylaldehyde, heptylaldehyde, octylaldehyde, nonylaldehyde, decylaldehyde, and other $C_{2-12}$ alkylmonoaldehydes, malonaldehyde, succinaldehyde, adipinaldehyde, sebacaldehyde, and other aliphatic polyaldehydes), aromatic aldehydes (e.g., benzaldehyde, anisaldehyde), alicyclic aldehydes (e.g., formylcyclohexane, cycloneral), and heterocyclic aldehydes (e.g., nicotinaldehyde, furfural).

As examples of the ketone, there may be mentioned aliphatic ketones (e.g., acetone, methyl ethyl ketone, methyl isopropyl ketone, methyl isobutyl ketone, methyl t-butyl ketone, 2-pentanone, 3-pentanone, 2-hexanone, 3-hexanone, 2-heptanone, 3-heptanone, 4-heptanone, 2-octanone, 3-octanone, 4-octanone, 2-nonanone, 2-decanone), aromatic ketones (e.g., acetophenone, propiophenone) and so on.

The illustrative carboxylic acid or its derivative includes aliphatic dicarboxylic acids or their derivatives (e.g., malonic acid or its ester, succinic acid or its ester, glutaric acid or its ester).

Oxidation reaction

The oxygen used in oxidation of the substrate may be active oxygen, but molecular oxygen is practically employed for economical advantages. Such molecular oxygen is not specifically limited, and use may be made of whichever of pure oxygen, or oxygen diluted with an inert gas such as nitrogen, helium, argon or carbon dioxide gas. Air is preferably employed from the viewpoints of handling property and safety, and economical property.

An amount of oxygen can be selected from a range according to the species of the substrate, and usually is, 0.5 mole or more (e.g., 1 mole or more), preferably about 1 to 100 moles, and more preferably about 2 to 50 moles relative to 1 mole of the substrate. The oxygen is practically used in an excess mole relative to the substrate. In specific, the reaction is advantageously carried out in an atmosphere containing molecular oxygen such as air or oxygen gas.

Oxidation process of the invention is generally conducted in an inert organic solvent. As the organic solvents, there may be mentioned, for example, formic acid, acetic acid, propionic acid and other organic carboxylic acids or hydroxycarboxylic acids, acetonitrile, propionitrile, benzonitrile and other nitriles, formaldehyde, acetamide, dimethylformamide (DMF), dimethylacetamide and other amides, t-butanol, t-amyl alcohol and other alcohols, hexane, octane and other aliphatic hydrocarbons, benzene and other aromatic hydrocarbons, chloroform, dichloromethane, dichloroethane, carbon tetrachloride, chlorobenzene and other halogenated hydrocarbons, nitrobenzene, nitromethane, nitroethane and other nitro compounds, ethyl acetate, butyl acetate and other esters, dimethyl ether, diethyl ether, diisopropyl ether, dioxane and other ethers, and mixtures of these solvents. Incidentally, the substrate may be employed as the reaction solvent, if used in an excess amount. Use may practically be made of, as the solvent, acetic acid or other organic acids, acetonitrile, benzonitrile or other nitriles.

The reaction in the presence of a proton acid results in smooth oxidation, and it provides an object compound with high selectivity in a high yield. The proton acid may also be used as the solvent as described above. As the proton acid, there may be exemplified organic acids (e.g., formic acid, acetic acid, propionic acid and other organic carboxylic acids, oxalic acid, succinic acid, tartaric acid and other hydroxycarboxylic acids, methanesulfonic acid, ethanesulfonic acid and other alkylsulfonic acids, benzenesulfonic acid, p-toluenesulfonic acid and other arylsulfonic acids), and inorganic acids (e.g., hydrochloric acid, sulfuric acid, nitric acid, phosphoric acid).

The process of the invention is characterized in that the oxidation reaction smoothly proceeds even in comparatively mild or moderate conditions. A reaction temperature can be voluntarily selected according to the species of the substrate and the catalytic system. The temperature is, for instance, about 0 to 300° C., preferably about 30 to 250° C., more preferably about 50 to 200° C., and practically about 70 to 150° C. As described above, depending on the species of the oxidation catalytic system, the oxidation reaction can smoothly proceed even at a comparatively low temperature such as room temperature. In the production of the adamantanepolyol, the reaction at a temperature of about 40 to 150° C., in particular about 60 to 120° C. (e.g., about 70 to 110° C.) insures formation of the adamantanepolyol in a short period.

The reaction may be carried out at ambient pressure (atmospheric pressure) or under a pressure (under a load). When the reaction is conducted under a pressure, the pressure is, usually, about 1 to 100 atm (e.g., about 1.5 to 80 atm), preferably about 2 to 70 atm, and more preferably about 5 to 50 atm. A reaction time can be liberally chosen within a range of about 30 minutes to 48 hours, preferably about 1 to 36 hours, and more preferably about 2 to 24 hours, according to the reaction temperature and pressure.

The reaction may be effected in a conventional manner such as in a batch system, semi-batch system or continuous system, in the presence of molecular oxygen or under flow of molecular oxygen. After completion of the reaction, a reaction product can easily be isolated and purified according to a conventional technology, such as filtration, condensation, distillation, extraction, crystallization, recrystallization, column chromatography, or other isolation means, or a combination of these technologies.

INDUSTRIAL APPLICABILITY OF THE INVENTION

The present invention does not specifically require treatment of an exhaust gas, and insures efficient oxidation of the substrate by means of oxidation with oxygen, or oxidation with air to give an oxide corresponding to the substrate with high efficiency. By way of illustration, the invention provides an oxide corresponding to the substrate with a high transformation rate and selectivity, by means of oxidation with molecular oxygen. Further, it insures direct and efficient production of a carboxylic acid (e.g., adipic acid or other long chain dicarboxylic acids, or an aromatic carboxylic acid) or a ketone (e.g., a cycloalkanone, a cycloalkenone, an aromatic ketone) from a corresponding substrate (a cycloalkane, a cycloalkene, an alkyl group-substituted aromatic compound) with a high transformation rate and selectivity.

Moreover, according to the invention, a methylidyne group in a bridgehead position or junction site of a polycyclic hydrocarbon can efficiently be oxidized with oxygen. Thus, a corresponding diol or higher polyol can be obtained from a condensed polycyclic hydrocarbon, or a bridged cyclic hydrocarbon with a high transformation rate and selectivity. Furthermore, the process of the invention insures introduction of a hydroxyl group into a tertiary carbon atom of a junction site of a polycyclic hydrocarbon with high efficiency, while inhibiting cleavage of the ring of the polycyclic hydrocarbon and by-production of a diketone. Thus, an adamantanediol, adamantanetriol or higher adamantanepolyol can effectively be obtained in a high yield by means of oxidation with oxygen.

EXAMPLES

The following examples are intended to describe the present invention in more detail, but should by no means be construed to limit the scope of the invention.

Example A1-1

To 25 milliliters of acetic acid were added 1.68 grams (20 millimoles) of cyclohexane, 0.26 gram (1.6 millimoles) of N-hydroxyphthalimide and 0.043 gram (0.12 millimole) of acetylacetonatomanganese $Mn(AA)_2$, and the resultant mixture was stirred under an oxygen atmosphere at a temperature of 100° C. for 6 hours. The products in the reaction mixture were analyzed by gas chromatography, and, as a result, cyclohexane was transformed into adipic acid with a transformation rate or conversion of 55% and selectivity of 82% (yield 45%). Formation of KA oil (cyclohexanone and cyclohexanol) was not recognized.

Example A2

The reaction was conducted in the same manner as Example A1-1 except using manganese oxide $MnO_2$ instead of acetylacetonatomanganese, and cyclohexane was transformed into adipic acid with a transformation rate of 50% and a yield of 42%. KA oil (cyclohexanone and cyclohexanol) was not observed.

Example A3

The procedure of Example A1-1 was repeated except that manganese chloride $MnCl_2$ was employed in lieu of acetylacetonatomanganese to obtain adipic acid with a transformation rate of cyclohexane of 55% and a yield of 43%. Formation of KA oil (cyclohexanone and cyclohexanol) was not recognized.

Example A4

By using manganese acetate $Mn(OAc)_2$ instead of acetylacetonatomanganese, the reaction was conducted in the same manner as Example A1-1. As a result, cyclohexane was transformed into adipic acid with a transformation rate of 60% and a yield of 50%. KA oil (cyclohexanone and cyclohexanol) was not observed.

Example A5

The reaction was carried out in the same manner as Example A1-1 except using benzonitrile as a solvent instead of acetic acid, and, as a result, cyclohexane was transformed into adipic acid with a transformation rate of 45% and a yield of 38%. The formation of KA oil (cyclohexanone and cyclohexanol) was not detected.

Example A6

The procedure of Example A1-1 was repeated except changing the oxygen gas pressure to 10 $kg/cm^2$, and, as a result, cyclohexane was transformed into adipic acid with a transformation rate of 75% and a yield of 54%. Formation of KA oil (cyclohexanone and cyclohexanol) was not observed.

Example A7

The reaction was effected in the same manner as Example A1-1 except that the reaction temperature was set at 120° C. to give adipic acid with a transformation rate of cyclohexane of 70% and a yield of 42%. Incidentally, KA oil was not observed to form.

Example A8

By using cyclohexanone instead of cyclohexane, the reaction was carried out in the same manner as Example A1-1. As a result, cyclohexanone was transformed into adipic acid with a transformation rate of 100% and a yield of 95%. The formation of KA oil (cyclohexanone and cyclohexanol) was not detected.

Example A9

The reaction procedure of Example A1-1 was repeated except that cyclohexanol was employed instead of cyclohexane and the stirring was conducted for 10 hours. As a result, cyclohexanol was transformed into adipic acid with a transformation rate of 95% and a yield of 90%. Meanwhile, the formation of KA oil (cyclohexanone and cyclohexanol) was not observed.

Example A10

Except that a mixture of cyclohexanone and cyclohexanol (50:50, by weight) was used in lieu of cyclohexane and the stirring was carried out for eight hours, the reaction was conducted in the same manner as Example A1-1. Adipic acid was obtained with a transformation rate of 95% and a yield of 90% without formation of KA oil.

Example A11

A mixture of 1.68 grams (20 millimoles) of cyclohexane, 0.26 gram (1.6 millimoles) of N-hydroxyphthalimide, 0.043 gram (0.12 millimole) of $Mn(AA)_2$, 0.06 gram (0.24 millimole) of acetylacetonatoiron $Fe(AA)_2$ and 25 ml of acetic acid was stirred in an oxygen atmosphere at 100° C. for six hours. As a result, cyclohexane was transformed into adipic acid with a transformation rate of 72% and in a yield of 65% (cyclohexane-based selectivity 91%). Further, glutaric acid was obtained with a yield of 5% (cyclohexane-based selectivity 7%).

Example A12

To 25 ml of acetic acid were added 1.68 grams (20 millimoles) of cyclohexane, 0.26 gram (1.6 millimoles) of N-hydroxyphthalimide, 0.005 gram (0.02 millimole) of $Mn(AA)_2$ and 0.02 gram (0.08 millimole) of $Fe(AA)_2$, and the resultant mixture was stirred in an oxygen atmosphere at 100° C. for six hours. As a result, cyclohexane was transformed into adipic acid with a transformation rate of 56% and a yield of 52% (cyclohexane-based selectivity 92%). Further, glutaric acid was produced in a yield of 3% (cyclohexane-based selectivity 5%).

Example A1-2

The reaction was conducted in the same manner as Example A1-1 except that the manganese compound was not used. Cyclohexane was transformed into adipic acid with a transformation rate of 56% and a yield of 10%. Incidentally, cyclohexanone and cyclohexanol were formed in yields of 36% and 4%, respectively.

Example B1-1

To 25 milliliters of benzonitrile were added 1.12 grams (10 millimoles) of cyclooctane, 0.13 gram (0.8 millimole) of N-hydroxyphthalimide and 0.015 gram (0.06 millimole) of acetylacetonatocobalt(III) $Co(AA)_3$, and the resultant mixture was stirred in an oxygen atmosphere at a temperature of 100° C. for 20 hours. Products in the reaction mixture were analyzed by gas chromatography. The result showed that cyclooctane was transformed, with a transformation rate of 94%, into cyclooctanone (yield 43%), cyclooctadione (yield 13%), suberic acid (yield 22%) and other products (yield 16%).

Example B1-2

The reaction procedure of Example B1-1 was repeated except using 0.015 gram (0.06 millimole) of acetylacetonatocobalt(II) $Co(AA)_2$ for 0.015 gram (0.06 millimole) of acetylacetonatocobalt(III) $Co(AA)_3$. As a result, cyclooctane was transformed, with a transformation rate of 99%, into cyclooctanone (yield 41%), cyclooctadione (yield 9%), suberic acid (yield 45%) and other products (yield 4%).

Example B2

The reaction was carried out in the same manner as Example B1-1, except that 0.021 gram (0.06 millimole) of acetylacetonatomanganese(II) $Mn(AA)_2$ was employed in lieu of 0.015 gram (0.06 millimole) of acetylacetonatocobalt (III) $Co(AA)_3$. As an outcome, cyclooctane was transformed into cyclooctanone (yield 6%), cyclooctadione (yield 10%), suberic acid (yield 74%) and other products (yield 4%) with a transformation rate of 94%.

Example B3

The procedure of Example B1-1 was repeated except using 10 millimoles of cyclononane instead of 10 millimoles of cyclooctane, and as a result, cyclononane was transformed into cyclononanone (yield 34%), azelaic acid (yield 56%) and other products (yield 3%) with a transformation rate of 93%. Cyclononadione was not detected.

Example B4

The reaction was conducted in the same manner as Example B1-1 except that 10 millimoles of cyclononane and 0.015 gram (0.06 millimole) of acetylacetonatocobalt(II) $Co(AA)_2$ were used instead of 10 millimoles of cyclooctane and 0.015 gram (0.06 millimole) of acetylacetonatocobalt (III) $Co(AA)_3$, respectively. Consequently, cyclononane was transformed into cyclononanone (yield 29%), azelaic acid (yield 66%) and other products (yield 4%) with a transformation rate of 99%, and cyclononadione was not detected.

Example B5

The reaction procedure of Example B1-1 was repeated except using 10 millimoles of cyclononane and 0.021 gram (0.06 millimoles) of acetylacetonatomanganese(II) $Mn(AA)_2$ instead of 10 millimoles of cyclooctane and 0.015 gram (0.06 millimole) of acetylacetonatocobalt (III) $Co(AA)_3$. As a result, cyclononane was transformed, with a transformation rate or conversion of 93%, into cyclononanone (yield 5%), azelaic acid (yield 83%) and other products (yield 5%). Cyclononadione was not detected.

The results of Examples B1 to B5 are set forth in Table 1.

TABLE 1

| | Substrate | Co-catalyst | Transformation rate (%) | Yield (%) | | | | Selectivity of monoketone and dicarboxylic acid |
|---|---|---|---|---|---|---|---|---|
| | | | | C1 | C2 | C3 | Others | |
| Example B1-1 | Cyclooctane | Co(III) | 94 | 43 | 13 | 22 | 16 | 69% |
| Example B1-2 | Cyclooctane | Co(II) | 99 | 41 | 9 | 45 | 4 | 87% |
| Example B2 | Cyclooctane | Mn(II) | 94 | 6 | 10 | 74 | 4 | 85% |
| Example B3 | Cyclononane | Co(III) | 93 | 34 | 0 | 56 | 3 | 97% |
| Example B4 | Cyclononane | Co(II) | 99 | 29 | 0 | 66 | 4 | 96% |
| Example B5 | Cyclononane | Mn(II) | 93 | 5 | 0 | 83 | 5 | 95% |

C1: monoketone,
C2: diketone,
C3: dicarboxylic acid

Example B6

A mixture of 1.12 grams (10 millimoles) of cyclooctane, 0.13 gram (0.8 millimole) of N-hydroxyphthalimide, 0.015 gram (0.06 millimole) of acetylacetonatocobalt(II) Co(AA)$_2$ and 25 milliliters of acetic acid was stirred in an oxygen atmosphere at a temperature of 120° C. for six hours. The analysis of the products in the reaction system with gas chromatography indicated that cyclooctane was transformed into suberic acid with a transformation rate of 95% (yield 70%).

Example B7

To 25 milliliters of acetic acid were added 1.26 grams (10 millimoles) of cyclononane, 0.13 gram (0.8 millimole) of N-hydroxyphthalimide and 0.015 gram (0.06 millimole) of Co(AA)$_2$, and the resultant mixture was stirred in an oxygen atmosphere at a temperature of 100° C. for six hours. Products in the reaction mixture were analyzed by means of gas chromatography, which showed that cyclononane was transformed into cyclononanone (yield 46%) and azelaic acid (yield 42%) with a transformation rate of 92%.

Example B8

A mixture of 1.40 grams (10 millimoles) of cyclodecane, 0.13 gram (0.8 millimole) of N-hydroxyphthalimide, 0.015 gram (0.06 millimole) of Co(AA)$_2$ and 25 milliliters of acetic acid was stirred in an oxygen atmosphere at a temperature of 100° C. for six hours. As a result, cyclodecane was transformed into cyclodecanone (yield 39%), sebacic acid (yield 48%) and cyclodecanedione (yield 5%) with a transformation rate of 96%.

Example B9

The reaction procedure of Example B8 was repeated except setting the reaction temperature at 90° C., and cyclodecane was transformed, with a transformation rate of 90%, into cyclodecanone (yield 64%), sebacic acid (yield 14%) and cyclodecanedione (yield 9%).

Example B10

The reaction was conducted in the same manner as Example B8 except setting the reaction temperature at 120° C. As a result, cyclodecane was transformed into cyclodecanone (yield 24%) and sebacic acid (yield 71%) with a transformation rate of 99%.

Example B11

The procedure of Example B8 was repeated except that 0.021 gram (0.06 millimole) of Mn(AA)$_2$ was used instead of 0.015 gram (0.06 millimole) of Co(AA)$_2$, and cyclodecane was transformed, with a transformation rate of 89%, into cyclodecanone (yield 4%) and sebacic acid (yield 82%).

Example B12

The reaction was carried out in the same manner as Example B8 except employing 1.54 grams (10 millimoles) of methylcyclodecane instead of 1.40 grams (10 millimoles) of cyclodecane. As a result, methylcyclodecane was transformed into 9-oxodecanoic acid (yield 67%) and 2-methylcyclodecanone (yield 15%) with a transformation rate of 85%.

Example B13

To 25 milliliters of acetic acid were added 1.68 grams (10 millimoles) of cyclododecane, 0.13 gram (0.8 millimole) of N-hydroxyphthalimide and 0.015 gram (0.06 millimole) of Co(AA)$_2$, and the resultant mixture was stirred in an oxygen atmosphere at a temperature of 100° C. for six hours. Consequently, cyclododecane was transformed, with a transformation rate of 96%, into cyclododecanone (yield 36%), dodecanedioic acid (yield 51%) and cyclododecanedione (yield 7%).

Example B14

The reaction procedure of Example B13 was repeated except using 0.021 gram (0.06 millimole) of Mn(AA)$_2$ instead of 0.015 gram (0.06 millimole) of Co(AA)$_2$ and stirring at 100° C. for eight hours. As a result, cyclododecane was transformed, with a transformation rate of 92%, into cyclododecanone (yield 2%), dodecanedioic acid (yield 84%) and cyclododecanedione (yield 6%).

Example B15

The reaction was effected in the same manner as Example B13 except that stirring was carried out at 85° C. for 6 hours, and as a result, cyclododecane was transformed into cyclododecanone (yield 69%), dodecanedioic acid (yield 12%) and cyclododecanedione (yield 3%) with a transformation rate of 84%.

Example B16

To 25 milliliters of acetic acid were added 1.96 grams (10 millimoles) of cyclotetradecane, 0.13 gram (0.8 millimole) of N-hydroxyphthalimide and 0.015 gram (0.06 millimole)

of Co(AA)$_2$, and the resultant mixture was stirred in an oxygen atmosphere at a temperature of 100° C. for six hours. As a result, cyclotetradecane was transformed into cyclotetradecanone (yield 32%), dodecanedicarboxylic acid (yield 52%) and cyclotetradecanedione (yield 8%) with a transformation rate of 92%.

Example C1

To 25 milliliters of acetonitrile were added 1.64 grams (20 millimoles) of cyclohexene, 0.26 gram (1.6 millimoles) of N-hydroxyphthalimide and 0.043 gram (0.12 millimole) of acetylacetonatocobalt Co(AA)$_2$. The resultant mixture was stirred in an oxygen atmosphere at 100° C. for 6 hours. The products in the reaction mixture were analyzed with gas chromatography, and cyclohexene was transformed, with a transformation rate of 90%, into 2-cyclohexen-1-one (selectivity based on cyclohexene 72%, yield 65%) and 2-cyclohexen-1-ol (selectivity based on cyclohexene 14%, yield 13%).

Example C2

The procedure of Example C1 was repeated except using cyclopentene instead of cyclohexene. Cyclopentene was transformed into 2-cyclopenten-1-one (cyclopentene-based selectivity 66%, yield 53%) and 2-cyclopenten-1-ol (cyclopentene-based selectivity 21%, yield 17%) with a transformation rate of 80%.

Example C3

A mixture of 1.10 grams (10 millimoles) of cyclooctene, 0.13 gram (0.8 millimole) of N-hydroxyphthalimide, 0.021 gram (0.06 millimole) of acetylacetonatocobalt Co(AA)$_2$ and 25 milliliters of acetonitrile was stirred in an oxygen atmosphere at a temperature of 100° C. for 6 hours. The product in the reaction mixture was analyzed with gas chromatography. Cyclooctene was transformed, with a transformation rate of 95%, into 2-cyclooctn-1-one (cyclooctene-based selectivity 82%, yield 78%) and 2-cyclooocten-1-ol (cyclooctene-based selectivity 16%, yield 15%).

Example C4

The reaction was conducted in the same manner as Example C1 except that acetic acid was employed for acetonitrile and the reaction temperature was set at 90° C. As a result, cyclohexene was transformed into 2-cyclohexen-1-one (cyclohexene-based selectivity 43%, yield 41%) and 1-acetyloxy-2-cyclohexene (cyclohexene-based selectivity 45%, yield 43%) with a transformation rate of 95%.

Comparative Example C1

To 25 milliliters of acetonitrile, were added 1.64 grams (20 millimoles) of cyclohexene, and azobisisobutyronitrile (5 mole percent). The resultant mixture was stirred in an oxygen atmosphere at a temperature of 90° C. for 4 hours. In analysis of the product in the reaction mixture with gas chromatography, cyclohexene was transformed into 2-cyclohexen-1-one (cyclohexene-based selectivity 12%, yield 4%) and 2-cyclohexen-1-ol (cyclohexene-based selectivity 3%, yield 1%) with a transformation rate of 34 percent.

Example D1-1

A mixture of 1.36 grams (10 millimoles) of adamantane, 0.13 gram (0.8 millimole) of N-hydroxyphthalimide, 0.015 gram (0.06 millimole) of acetylacetonatocobalt(III) (Co(AA)$_3$) and 25 milliliters of acetic acid was stirred under an oxygen atmosphere at a temperature of 90° C. for eight hours. As a result, adamantane was transformed, at a transformation rate of 65%, into 1-adamantanol (adamantane-based selectivity 71%, yield 46%), 1,3-adamantanediol (adamantane-based selectivity 17%, yield 11%) and 2-adamantanone (adamantane-based selectivity 9%, yield 6%). The selectivity for the alcohols was 89%.

Examples D2-1 to D7-1

The procedure of Example D1-1 was repeated except that the reaction was carried out in the conditions shown in Table 2. Results are set forth in Table 2.

In Table 2, the symbols "C-1," "C-2" and "C-3" respectively mean 1-adamantanol, 1,3-adamantanediol and 2-adamantanone.

Most of the "Other" products in Table 2 were keto-alcohols of adamantane.

Examples D1-2 to D6-2

The reaction was conducted in the same manner as Examples D2-1 to D7-1 except using 0.015 gram of acetylacetonatocobalt(II) Co(AA)$_2$ instead of 0.015 gram of acetylacetonatocobalt(III) Co(AA)$_3$ to give results shown in Table 2.

Example D7-2

The procedure of Example D4-2 was repeated except using benzonitrile instead of acetic acid. The results are set forth in Table 2.

Incidentally, almost all of the "Other" products in the examples of Table 2 were 1,3,5-adamantanetriol and 1,3,5,7-adamantanetetraol, and keto-alcohol was not detected.

TABLE 2

| | Co-catalyst | Reaction temperature (° C.) | Reaction time (hr) | Solvent | Transformation rate (%) | Yield (%) | | | | Selectivity for alcohol |
| --- | --- | --- | --- | --- | --- | --- | --- | --- | --- | --- |
| | | | | | | C-1 | C-2 | C-3 | Other | |
| Example D2-1 | Co(III) | 65 | 6 | AcOH | 37 | 33 | 0 | 2 | 2 | 89% |
| Example D1-2 | Co(II) | 65 | 6 | AcOH | 55 | 37 | 15 | 1 | 2 | 98% |
| Example D3-1 | Co(III) | 75 | 3 | AcOH | 40 | 34 | 1 | 3 | 2 | 88% |
| Example D2-2 | Co(II) | 75 | 3 | AcOH | 65 | 48 | 13 | 2 | 2 | 97% |
| Example D4-1 | Co(III) | 75 | 6 | AcOH | 66 | 49 | 9 | 6 | 2 | 88% |
| Example D3-2 | Co(II) | 75 | 6 | AcOH | 98 | 33 | 55 | 4 | 6 | 96% |
| Example D5-1 | Co(II) | 75 | 10 | AcOH | 92 | 50 | 20 | 18 | 4 | 76% |
| Example D4-2 | Co(II) | 75 | 10 | AcOH | 99 | 26 | 58 | 3 | 12 | 97% |

TABLE 2-continued

|  | Co-catalyst | Reaction temperature (° C.) | Reaction time (hr) | Solvent | Transformation rate (%) | Yield (%) C-1 | C-2 | C-3 | Other | Selectivity for alcohol |
|---|---|---|---|---|---|---|---|---|---|---|
| Example D6-1 | Co(III) | 85 | 6 | AcOH | 91 | 42 | 26 | 18 | 5 | 75% |
| Example D5-2 | Co(II) | 85 | 6 | AcOH | 99 | 27 | 58 | 5 | 9 | 95% |
| Example D7-1 | Co(III) | 95 | 6 | AcOH | 99 | 36 | 40 | 16 | 7 | 77% |
| Example D6-2 | Co(II) | 95 | 6 | AcOH | 99 | 19 | 58 | 7 | 15 | 93% |
| Example D7-2 | Co(II) | 75 | 10 | φCN | 55 | 33 | 16 | 4 | 2 | 93% |

C-1: 1-adamantanol,
C-2: 1,3-adamantanediol,
C-3: 2-adamantanone
AcOH: acetic acid,
φCN: benzonitrile

Example D8

A mixture of 1.64 grams (10 millimoles) of 1,3-dimethyladamantane, 0.13 gram (0.8 millimole) of N-hydroxyphthalimide, 0.015 gram (0.06 millimole) of Co(AA)$_2$ and 10 milliliters of acetic acid was stirred under oxygen atmosphere at a temperature of 70° C. for six hours. As a result, with a transformation rate for 1,3-dimethyladamantane of 99%, 1-hydroxy-3,5-dimethyladamantane (yield 39%), and 1,3-dihydroxy-5,7-dimethyladamantane (yield 58%) were obtained. The selectivity for the alcohols was 97%.

Example D9

The reaction was effected in the same manner as Example D8 except setting the reaction temperature at 60° C., and 1,3-dimethyladamantane was transformed into 1-hydroxy-3,5-dimethyladamantane (yield 49%) and 1,3-dihydroxy-5,7-dimethyladamantane (yield 22%) with a transformation rate of 74%. The selectivity for the alcohols was 96%.

Example D10

To 25 milliliters of acetic acid were added 1.52 grams (10 millimoles) of 1-adamantanol, 0.13 gram (0.8 millimole) of N-hydroxyphthalimide and 0.015 gram (0.06 millimole) of Co(AA)$_2$, and the resultant mixture was stirred under an oxygen atmosphere at a temperature of 75° C. for three hours. As a result, 1-adamantanol was transformed, with a transformation rate of 80%, into 1,3-adamantanediol (selectivity for 1-adamantanol 66%, yield 53%) and 1,3,5-adamantanetriol (selectivity for 1-adamantanol 33%, yield 26%), with a selectivity for the alcohols of 99%.

Example D11

The reaction procedure of Example D10 was repeated except stirring at temperature of 85° C. for 6 hours to give 1,3-adamantanediol (selectivity for 1-adamantanol 42%, yield 42%), 1,3,5-adamantanetriol (selectivity for 1-adamantanol 46%, yield 46%) and 1,3,5,7-adamantanetetraol (selectivity for 1-adamantanol 10%, yield 10%) with a transformation rate for 1-adamantanol of 99%. The selectivity for the alcohols was 99%.

Example D12

The reaction was conducted in the same manner as Example D10 except that the stirring was effected at a temperature of 95° C. for 6 hours to provide 1,3-adamantanediol (selectivity for 1-adamantanol of 22%, yield 22%), 1,3,5-adamantanetriol (selectivity for 1-adamantanol of 41%, yield 41%) and 1,3,5,7-adamantanetetraol (selectivity for 1-adamantanol of 36%, yield 36%) with a transformation rate for 1-adamantanol of 99%. The selectivity of the alcohols was 99%.

Example D13

A mixture of 1.68 grams (10 millimoles) of 1,3-adamantanediol, 0.13 gram (0.8 millimole) of N-hydroxyphthalimide, 0.015 gram (0.06 millimole) of Co(AA)$_2$ and 25 milliliters of acetic acid was stirred under an oxygen atmosphere at a temperature of 95° C. for 6 hours. Thus, 1,3-adamantanediol was transformed, with a transformation rate of 99%, into 1,3,5-adamantanetriol (selectivity for 1,3-adamantanediol 37%, yield 37%) and 1,3,5,7-adamantanetetraol (selectivity for 1,3-adamantanediol 62%, yield 62%). The selectivity for the alcohols was 99%.

Example D14

To 25 milliliters of benzonitrile were added 0.68 gram (5 millimoles) of adamantane, 0.76 gram (5 millimoles) of 1-adamantanol, 0.13 gram (0.8 millimole) of N-hydroxyphthalimide and 0.015 gram (0.06 millimole) of Co(AA)$_2$, and the resultant mixture was stirred in an oxygen atmosphere at a temperature of 85° C. for 6 hours. As a result, 1-adamantanol (yield 33%), 1,3-adamantanediol (yield 41%) and 1,3,5-adamantanetriol (yield 21%) were produced with a transformation rate for adamantane of 91%. The selectivity for the alcohols was 99%.

Example D15

A mixture of 0.96 gram (10 millimoles) of norbornane, 0.13 gram (0.8 millimole) of N-hydroxyphthalimide, 0.015 gram (0.06 millimole) of Co(AA)$_2$ and 10 milliliters of acetic acid was stirred in an oxygen atmosphere at a temperature of 75° C. for 15 hours to give 1-hydroxynorbornane (selectivity for norbornane 44%, yield 44%) and 1,2-dihydroxynorbornane (selectivity for norbornane 55%, yield 55%) with a transformation rate of norbornane of 99% and the selectivity for the alcohols of 99%.

Example D16

To 10 milliliters of acetic acid were added 1.5 grams (10 millimoles) of tricyclo[4.3.1.1$^{2,5}$]undecane, 0.13 gram (0.8 millimole) of N-hydroxyphthalimide and 0.015 gram (0.06 millimole) of Co(AA)$_2$, and the resultant mixture was stirred under an oxygen atmosphere at 75° C. for 15 hours. As a result, tricyclo[4.3.1.1$^{2,5}$]undecane was transformed, with a transformation rate of 99%, into 1-hydroxytricyclo

[4.3.1.1$^{2,5}$]undecane (selectivity for tricyclo[4.3.1.1$^{2,5}$] undecane 24%, yield 24%) and dihydroxy-tricyclo[4.3.1.1$^{2,5}$]undecane (selectivity for tricyclo[4.3.1.1$^{2,5}$]undecane 75%, yield 75%). A selectivity for the alcohols was 99 percent.

Example D17

To 25 milliliters of acetonitrile were added 1.38 grams (10 millimoles) of pinane, 0.13 gram (0.8 millimole) of N-hydroxyphthalimide and 0.015 gram (0.06 millimole) of Co(AA)$_2$, and the resultant mixture was stirred in an oxygen atmosphere at a temperature of 100° C. for six hours. Pinane was transformed into 2-pinanol (selectivity for pinane 91%, yield 82%) with a transformation rate of 90%.

Example D18

A mixture of 1.38 grams (10 millimoles) of cis-decalin, 0.16 gram (1.0 millimole) of N-hydroxyphthalimide, 0.007 gram (0.05 millimole) of MoO$_3$ and 10 milliliters of acetic acid was stirred at a temperature of 50° C. for 6 hours under an oxygen atmosphere. Cis-decalin was transformed, with a transformation rate of 65%, into 1-hydroxy-cis-decalin (selectivity for cis-decalin 71%, yield 46%), 1,6-dihydroxy-cis-decalin (selectivity for cis-decalin 17%, yield 11%), hydroxy-cis-decalin oxidized at a methylene position (selectivity for cis-decalin 6%, yield 4%) and 1,6-decanedione (selectivity for consumed cis-decalin 5%, yield 3%). The selectivity for the alcohols was 94%.

Example D19

To 10 milliliters of benzonitrile were added 1.38 grams (10 millimoles) of cis-decalin, 0.16 gram (1.0 millimole) of N-hydroxyphthalimide, 0.007 gram (0.05 millimole) of MoO$_3$, and the resultant mixture was stirred under an oxygen atmosphere at a temperature of 75° C. for six hours. As a result, cis-decalin was transformed, with a transformation rate of 85%, into 1-hydroxy-cis-decalin (selectivity for cis-decalin 72%, yield 61%), 1,6-dihydroxy-cis-decalin (selectivity for cis-decalin 21%, yield 18%), hydroxy-cis-decalin which had been oxidized at a methylene position (selectivity for cis-decalin 2%, yield 2%), and 1,6-decanedione (selectivity for cis-decalin 4%, yield 3%) with a selectivity for the alcohols of 95%.

Example D20

A mixture of 1.38 grams (10 millimoles) of cis-decalin, 0.16 gram (1.0 millimole) of N-hydroxyphthalimide, 0.007 gram (0.05 millimole) of MoO$_3$ and 10 milliliters of acetic acid was stirred at a temperature of 75° C. for 6 hours in an oxygen atmosphere. As a result, cis-decalin was transformed, with a transformation rate of 91%, into 1-hydroxy-cis-decalin (selectivity for cis-decalin 66%, yield 60%), 1,6-dihydroxy-cis-decalin (selectivity for cis-decalin 21%, yield 19%), hydroxy-cis-decalin oxidized at a methylene position (selectivity for cis-decalin 4%, yield 4%), and 1,6-decanedione (selectivity for cis-decalin 9%, yield 8%) with a selectivity for the alcohols of 91%.

Example D21

To 10 milliliters of benzonitrile were added 1.38 grams (10 millimoles) of cis-decalin, 0.16 gram (1.0 millimole) of N-hydroxyphthalimide, and 0.017 gram (0.05 millimole) of acetylacetonatomanganese Mn(AA)$_3$, and the resultant mixture was stirred in an oxygen atmosphere at a temperature of 75° C. for 6 hours. As a result, cis-decalin was transformed, with a transformation rate of 75%, into 1-hydroxy-cis-decalin (selectivity for cis-decalin 71%, yield 55%), 1,6-dihydroxy-cis-decalin (selectivity for cis-decalin 16%, yield 12%), hydroxy-cis-decalin oxidized at a methylene position (selectivity for cis-decalin 4%, yield 3%) and 1,6-decanedione (selectivity for cis-decalin 5%, yield 4%) with a selectivity of the alcohols of 93%.

Example D22

Under an oxygen atmosphere, a mixture of 1.36 grams (10 millimoles) of endotricyclo[5.2.1.0$^{2,6}$]decane, 0.16 gram (1.0 millimole) of N-hydroxyphthalimide, 0.007 gram (0.05 millimole) of MoO$_3$ and 10 milliliters of acetic acid was stirred at a temperature of 65° C. for 6 hours. As a result, endotricyclo[5.2.1.0$^{2,6}$]decane was transformed, with a transformation rate of 51%, into 2-hydroxyendotricyclo[5.2.1.0$^{2,6}$]decane (selectivity for the substrate 45%, yield 23%), 2,6-dihydroxyendotricyclo[5.2.1.0$^{2,6}$]decane (selectivity for the substrate 49%, yield 25%) and dicyclo[5.2.1]decane-2,6-dione (selectivity for the substrate 4%, yield 2%). A selectivity for the alcohols was 94%.

Example D23

To 10 milliliters of acetic acid were added 1.36 grams (10 millimoles) of exotricyclo[5.2.1.0$^{2,6}$]decane, 0.16 gram (1.0 millimole) of N-hydroxyphthalimide and 0.007 gram (0.05 millimole) of MoO$_3$, and the resultant mixture was stirred at a temperature of 65° C. for 6 hours in an oxygen atmosphere. Thus, exotricyclo[5.2.1.0$^{2,6}$]decane was transformed, with a transformation rate of 43%, into 2-hydroxyexotricyclo[5.2.1.0$^{2,6}$]decane (selectivity for the substrate 72%, yield 31%), 2,6-dihydroxyexotricyclo[5.2.1.0$^{2,6}$]decane (selectivity for the substrate 23%, yield 10%) and dicyclo[5.2.1]decane-2,6-dione (selectivity for the substrate 5%, yield 2%) with a selectivity of the alcohols of 95%.

Example D24

A mixture of 1.62 grams (10 millimoles) of tetracyclo[4.4.0.1$^{2,5}$.1$^{7,10}$]dodecane, 0.16 gram (1.0 millimole) of N-hydroxyphthalimide, 0.007 gram (0.05 millimole) of MoO$_3$ and 10 milliliters of acetic acid was stirred at a temperature of 75° C. for 6 hours in an oxygen atmosphere. As a result, tetracyclo[4.4.0.1$^{2,5}$.1$^{7,10}$]dodecane was transformed, with a transformation rate of 55%, into 1-hydroxytetracyclo[4.4.0.1$^{2,5}$.1$^{7,10}$]dodecane (selectivity for the substrate 67%, yield 37%), 1,6-dihydroxytetracyclo[4.4.0.1$^{2,5}$.1$^{7,10}$]dodecane (selectivity for the substrate 18%, yield 10%) and tricyclo[6.2.1.1$^{3,0}$]dodecane-2,7-dione (selectivity for the substrate 13%, yield 7%). A selectivity for the alcohols was 85%.

Example D25

To 10 milliliters of acetic acid were added 1.26 grams (10 millimoles) of cis-perhydroindane, 0.16 gram (1.0 millimole) of N-hydroxyphthalimide and 0.007 gram (0.05 millimole) of MoO$_3$, and the resultant mixture was stirred at 75° C. for 6 hours in an oxygen atmosphere.

Thus, cis-perhydroindane was transformed, with a transformation rate of 87%, into 1-hydroxy-cis-perhydroindane (selectivity for the substrate 62%, yield 54%), 1,6-dihydroxy-cis-perhydroindane (selectivity for the substrate 31%, yield 27%), hydroxy-cis-perhydroindane oxidized at a methylene position (selectivity for the substrate 3%, yield 2%) and 1,6-nonanedione (selectivity for the substrate 5%, yield 4%) with a selectivity for the alcohols of 95%.

Example D26

The reaction was conducted in the same manner as Example D18 except that the mixture was stirred at 140° C. for 6 hours. As a result, cis-decalin was transformed, with a transformation rate of 95%, into 1-hydroxy-cis-decalin (selectivity for the substrate 18%, yield 17%), 1,6-dihydroxy-cis-decalin (selectivity for the substrate 3%, yield 3%) and 1,6-decanedione (selectivity for the substrate 73%, yield 69%) with a selectivity of the alcohols of 21%.

Example D27

To 25 milliliters of acetic acid were added 10 millimoles of adamantane, 1 millimole of N-hydroxyphthalimide and 0.05 millimole of acetylacetonatocopper(II) $Cu(AA)_2$. In an oxygen atmosphere, the resultant mixture was stirred at a temperature of 75° C. for 6 hours. Adamantane was transformed, with a transformation rate of 53%, into 1-adamantanol (yield 50%) and 2-adamantanone (yield 4%). The selectivity for the alcohol and ketone was 97%.

Example D28

A mixture of 10 millimoles of adamantane, 1 millimole of N-hydroxyphthalimide, 0.05 millimole of acetylacetonatozirconium(IV) $Zr(AA)_4$ and 25 milliliters of acetic acid was stirred at a temperature of 75° C. for 6 hours in an oxygen atmosphere. Adamantane was transformed into 1-adamantanol (yield 28%), 1,3-adamantanediol (yield 6%) and 2-adamantanone (yield 3%) with a transformation rate of 43%.

Example D29

To 25 milliliters of acetic acid were added 10 millimoles of adamantane, 1 millimole of N-hydroxyphthalimide and 0.05 millimole of zirconyl acetate $ZrO(OAc)_2$. The resultant mixture was stirred at a temperature of 75° C. for 6 hours in an oxygen atmosphere. As a result, adamantane was transformed into 1-adamantanol (yield 42%), 1,3-adamantanediol (yield 31%) and 2-adamantanone (yield 7%) with a transformation rate of 91 percent.

Example D30

A mixture of 10 millimoles of adamantane, 1 millimole of N-hydroxyphthalimide and 0.05 millimole of vanadylacetylacetonato $VO(AA)_2$ was stirred at a temperature of 75° C. for 6 hours in an oxygen atmosphere. As a result, adamantane was transformed into 1-adamantanol (yield 25%), 1,3-adamantanediol (yield 34%), adamantanetriol (yield 6%) and adamantanetetraol (yield 6%) with a transformation rate of 98 percent.

Example D31

The reaction was conducted in the same manner as Example D30 except using 0.05 millimole of acetylacetonatovanadium $V(AA)_3$ in lieu of vanadylacetylacetonato $VO(AA)_2$. As a result, adamantane was transformed, with a transformation rate of 99 percent, into 1-adamantanol (yield 27%), 1,3-adamantanediol (yield 34%), adamantanetriol (yield 6%) and adamantanetetraol (yield 7%).

Example D32

The procedure of Example D30 was repeated except that 0.05 millimole of vanadium oxide $V_2O_5$ was employed instead of vanadylacetylacetonato $VO(AA)_2$. As a result, adamantane was transformed into 1-adamantanol (yield 24%), 1,3-adamantanediol (yield 35%), adamantanetriol (yield 6%) and adamantanetetraol (yield 8%) with a transformation rate of 99 percent.

Example D33

The reaction was carried out in the same manner as Example D30 except using 0.05 millimole of vanadium oxide $V_2O_3$ instead of vanadylacetylacetonato $VO(AA)_2$. With a transformation rate of 99%, adamantane was transformed into 1-adamantanol (yield 23%), 1,3-adamantanediol (yield 36%), adamantanetriol (yield 8%) and adamantanetetraol (yield 8%).

Example D34

By using vanadyl chloride $VOCl_2$ instead of vanadylacetylacetonato $VO(AA)_2$, the reaction was conducted in the same manner as Example D30. As a result, adamantane was transformed, with a transformation rate of 98%, into 1-adamantanol (yield 28%), 1,3-adamantanediol (yield 32%), adamantanetriol (yield 5%) and adamantanetetraol (yield 4%).

Example D35

To 25 milliliters of acetic acid were added 10 millimoles of adamantane, 2 millimoles of N-hydroxyphthalimide, and 0.1 millimole of acetylacetonatovanadium $V(AA)_3$. The resultant mixture was stirred at a temperature of 85° C. for 10 hours in an oxygen atmosphere. As a result, adamantane was transformed into 1-adamantanol (yield 8%), 1,3-adamantanediol (yield 22%), adamantanetriol (yield 33%) and adamantanetetraol (yield 20%) with a transformation rate of 99 percent.

Example D36

The reaction was carried out in the same manner as Example D35, except employing 0.1 millimole of acetylacetonatomanganese $Mn(AA)_3$ for acetylacetonatovanadium $V(AA)_3$. As a result, adamantane was transformed, with a transformation rate of 97%, into 1-adamantanol (yield 49%), 1,3-adamantanediol (yield 24%), adamantanetriol (yield 3%) and adamantanetetraol (yield 2%).

Example D37

By using 0.1 millimole of molybdic acid $H_2MoO_4$ in lieu of acetylacetonatovanadium $V(AA)_3$, the reaction was carried out in the same manner as Example D35. Adamantane was transformed into 1-adamantanol (yield 57%), 1,3-adamantanediol (yield 22%), adamantanetriol (yield 3%) and adamantanetetraol (yield 3%) with a transformation rate of 99 percent.

Example D38

The procedure of Example D35 was repeated except that 0.1 millimole of acetylacetonatocopper(II) $Cu(AA)_2$ was employed instead of acetylacetonatovanadium $V(AA)_3$. As a result, adamantane was transformed, with a transformation rate of 49%, into 1-adamantanol (yield 42%) and 1,3-adamantanediol (yield 6%).

Example D39

The reaction was conducted in the same manner as Example D35, except using 0.1 millimole of acetylacetonatozinc(II) $Zn(AA)_2$ instead of acetylacetonatovanadium $V(AA)_3$. Thus, with a transformation rate of 40%, adamantane was transformed into 1-adamantanol (yield 30%) and 1,3-adamantanediol (yield 7%).

Example D40

By employing 0.1 millimole of acetylacetonatoaluminium (III) Al(AA)$_3$ instead of acetylacetonatovanadium V(AA)$_3$, the reaction was conducted in the same manner as Example D35. Adamantane was transformed into 1-adamantanol (yield 10%) and 1,3-adamantanediol (yield 2%) with a transformation rate of 15 percent.

Example D41

The procedure of Example D35 was repeated except that 0.1 millimole of acetylacetonatomagnesium(II) Mg(AA)$_2$ instead of acetylacetonatovanadium V(AA)$_3$. As a result, adamantane was transformed into 1-adamantanol (yield 13%) and 1,3-adamantanediol (yield 2%) with a transformation rate of 22 percent.

Example D42

A reaction was carried out in the same manner as Example D35, except using 0.1 millimole of samarium iodide SmI$_2$ in lieu of acetylacetonatovanadium V(AA)$_3$. With a transformation rate of 34%, adamantane was transformed into 1-adamantanol (yield 22%) and 1,3-adamantanediol (yield 4%).

Example E1

To 25 milliliters of acetic acid were added 0.921 gram (10 millimoles) of toluene, 0.16 gram (1 millimole) of N-hydroxyphthalimide and 0.015 gram (0.05 millimole) of acetylacetonatocobalt(II) Co(AA)$_2$, and the resultant mixture was stirred in an oxygen atmosphere at a temperature of 100° C. for 6 hours. The products in the reaction mixture were analyzed by gas chromatography, according to which toluene was transformed into benzoic acid with a transformation rate of 95% and a yield of 95% (selectivity 100%).

Example E2

The reaction was conducted in the same manner as Example E1 except that the stirring was carried out at a temperature of 100° C. for four hours. Toluene was transformed into benzoic acid at a transformation rate of 93% and a yield of 92% (selectivity 99%).

Example E3

A mixture of 1.06 grams (10 millimoles) of p-xylene, 0.32 gram (2 millimoles) of N-hydroxyphthalimide, 0.018 gram (0.05 millimole) of acetylacetonatocobalt(III) Co(AA)$_3$ and 25 milliliters of acetic acid was stirred in an oxygen atmosphere at a temperature of 100° C. for 12 hours. As a result, p-xylene was transformed into terephthalic acid (yield 71%) and p-methylbenzoic acid (yield 24%) with a transformation rate of 99%.

Example E4

The reaction was carried out in the same manner as Example E3 except that the stirring was effected at 100° C. for 6 hours, and, as a result, p-xylene was transformed into terephthalic acid (yield 9%) and p-methylbenzoic acid (yield 76%) with a transformation rate of 99 percent.

Example E5

To 25 milliliters of acetic acid were added 1.06 grams (10 millimoles) of p-xylene, 0.16 gram (1 millimole) of N-hydroxyphthalimide and 0.018 gram (0.05 millimole) of acetylacetonatocobalt(II) Co(AA)$_2$, and the resultant mixture was stirred in an oxygen atmosphere at a temperature of 100° C. for 12 hours. With a transformation rate of 99 percent, p-xylene was transformed into terephthalic acid (yield 70%) and p-methylbenzoic acid (yield 27%).

Example E6

The procedure of Example E5 was repeated except that the stirring was effected at a temperature of 100° C. for 6 hours. As a result, p-xylene was transformed into terephthalic acid (yield 57%) and p-methylbenzoic acid (yield 42%) with a transformation rate of 99 percent.

Example E7

To 25 milliliters of acetic acid were added 1.06 grams (10 millimoles) of o-xylene, 0.16 gram (1 millimole) of N-hydroxyphthalimide and 0.018 gram (0.05 millimole) of acetylacetonatocobalt(II) Co(AA)$_2$, and the resultant mixture was stirred in an oxygen atmosphere at a temperature of 100° C. for 6 hours. With a transformation rate of 98%, o-xylene was transformed into phthalic acid (yield 40%), o-methylbenzoic acid (yield 46%) and phthalic anhydride (yield 10%).

Example E8

In an oxygen atmosphere, a mixture of 1.06 grams (10 millimoles) of o-xylene, 0.16 gram (1 millimole) of N-hydroxyphthalimide, 0.018 gram (0.05 millimole) of acetylacetonatocobalt(III) Co(AA)$_3$ and 25 milliliters of acetic acid was stirred at a temperature of 100° C. for 6 hours. As a result, o-xylene was transformed into phthalic acid (yield 18%) and o-methylbenzoic acid (yield 71%) with a transformation rate of 92%.

Example E9

To 25 milliliters of acetic acid were added 1.49 grams (10 millimoles) of 4-t-butyl-1-methylbenzene, 0.16 gram (1 millimole) of N-hydroxyphthalimide and 0.018 gram (0.05 millimole) of acetylacetonatocobalt(III) Co(AA)$_3$, and the resultant mixture was stirred in an oxygen atmosphere at 100° C. for 6 hours. With a transformation rate of 95%, 4-t-butyl-1-methylbenzene was transformed into 4-t-butylbenzoic acid (yield 88%).

Example E10

A mixture of 1.49 grams (10 millimoles) of 4-t-butyl-1-methylbenzene, 0.03 gram (0.2 millimole) of N-hydroxyphthalimide, 0.018 gram (0.05 millimole) of acetylacetonatocobalt(III) Co(AA)$_3$ and 25 milliliters of acetic acid was stirred in an oxygen atmosphere at 100° C. for 12 hours. As a result, 4-t-butyl-1-methylbenzene was transformed into 4-t-butylbenzoic acid (yield 64%) with a transformation rate of 70 percent.

Example E11

In an oxygen atmosphere, a mixture of 1.49 grams (10 millimoles) of 4-t-butyl-1-methylbenzene, 0.16 gram (1 millimole) of N-hydroxyphthalimide, 0.018 gram (0.05 millimole) of acetylacetonatocobalt(II) Co(AA)$_2$ and 25 milliliters of acetic acid was stirred at a temperature of 100° C. for 6 hours. With a transformation rate of 99%, 4-t-butyl-1-methylbenzene was transformed into 4-t-butylbenzoic acid (yield 94%).

Example E12

To 25 ml of acetic acid were added 1.23 grams (10 millimoles) of 4-methoxy-1-methylbenzene, 0.16 gram (1 millimole) of N-hydroxyphthalimide and 0.018 gram (0.05 millimole) of acetylacetonatocobalt(II) Co(AA)$_2$, and the resultant mixture was stirred in an oxygen atmosphere at 100° C. for 6 hours. As a result, 4-methoxy-1-methylbenzene was transformed into 4-methoxybenzoic acid (yield 93%) with a transformation rate of 99 percent.

Example E13

The reaction was carried out in the same manner as Example E12 except using 10 millimoles of 4-acetyloxy-1-methylbenzene instead of 10 millimoles of 4-methoxy-1-methylbenzene. As a result, the substrate was transformed into 4-acetyloxybenzoic acid (yield 92%) with a transformation rate of 95%.

Example E14

By using 10 millimoles of p-cresol instead of 10 millimoles of 4-methoxy-1-methylbenzene, and 25 milliliters of benzonitrile in lieu of 25 milliliters of acetic acid, the reaction was conducted in the same manner as Example E12. The substrate was transformed into 4-hydroxybenzoic acid (yield 18%) and 4-hydroxybenzaldehyde (yield 37%) with a transformation rate of about 70%.

Example E15

The reaction procedure of Example E12 was repeated except employing 10 millimoles of 2-methylfuran instead of 10 millimoles of 4-methoxy-1-methylbenzene. As a result, the substrate was transformed into furan-2-carboxylic acid (yield 88%) with a transformation rate of 92%.

Example E16

By using 10 millimoles of 2-methylpyran instead of 10 millimoles of 4-methoxy-1-methylbenzene, the reaction was conducted in the similar manner to that of Example E12, and, as a result, pyran-2-carboxylic acid (yield 83%) was produced with a transformation rate of the substrate of 85%.

Example E17

To 25 milliliters of acetic acid were added 10 millimoles of toluene, 1 millimole of N-hydroxyphthalimide and 0.05 millimole of acetylacetonatochromium(III) Cr(AA)$_3$. The resultant mixture was stirred at 70° C. for 6 hours in an oxygen atmosphere. As a result, toluene was transformed into benzoic acid (yield 37%) with a transformation rate of 42 percent.

Example E18

Ten (10) millimoles of toluene, 1 millimole of N-hydroxyphthalimide, 0.05 millimole of acetylacetonatonickel(II) Ni(AA)$_2$ and 25 milliliters of acetic acid were mixed, and the resultant mixture was stirred in an oxygen atmosphere at 70° C. for 6 hours. With a transformation rate of 37 percent, toluene was transformed into benzoic acid (yield 32%).

Example E19

To 25 milliliters of acetic acid were added 10 millimoles of toluene, 1 millimole of N-hydroxyphthalimide and 0.05 millimole of acetylacetonatovanadium(III) V(AA)$_3$. The resultant mixture was stirred at a temperature of 70° C. for 8 hours in an oxygen atmosphere, and toluene was transformed into benzoic acid (yield 68%) with a transformation rate of 80 percent.

Example E20

In an oxygen atmosphere, a mixture of 10 millimoles of ethylbenzene, 1 millimole of N-hydroxyphthalimide, 0.05 millimole of acetylacetonatovanadium(III) V(AA)$_3$ and 25 milliliters of acetic acid was stirred at 75° C. for 8 hours in an oxygen atmosphere. Ethylbenzene was transformed into acetophenone (yield 76%) with a transformation rate of 84 percent.

Example E21

To 25 milliliters of acetonitrile were added 10 millimoles of durene, 1 millimole of N-hydroxyphthalimide and 0.05 millimole of copper acetate (Cu(OAc)$_2$). The resultant mixture was stirred at 70° C. for three hours in an oxygen atmosphere. With a transformation rate of 95%, durene was transformed into 2,4,5-trimethylbenzoic acid (yield 59%).

Example E22

A mixture of 10 millimoles of durene, 1 millimole of N-hydroxyphthalimide, 0.05 millimole of acetylacetonatomanganese(II) Mn(AA)$_2$ and 25 milliliters of acetonitrile was stirred, in an oxygen atmosphere, at a temperature of 70° C. for 3 hours. As a result, durene was transformed into 2,4,5-trimethylbenzoic acid (yield 57%) with a transformation rate of 94%.

Example E23

To 25 milliliters of acetic acid were added 10 millimoles of durene, 1 millimole of N-hydroxyphthalimide and 0.05 millimole of acetylacetonatocobalt(II) Co(AA)$_2$, and the resultant mixture was stirred at a temperature of 60° C. for 3 hours in an oxygen atmosphere. As a result, durene was transformed, with a transformation rate of about 100%, into 2,4,5-trimethylbenzoic acid (yield 87%).

Example E24

Ten (10) millimoles of durene, 1 millimole of N-hydroxyphthalimide, 0.05 millimole of acetylacetonatocobalt(II) Co(AA)$_2$ and 25 milliliters of acetic acid were mixed, and the resultant mixture was stirred at room temperature (about 20° C.) for 12 hours in an oxygen atmosphere. With a transformation rate of about 100 percent, durene was transformed into 2,4,5-trimethylbenzoic acid (yield 87%).

Example E25

To 25 milliliters of acetic acid were added 10 millimoles of durene, 1 millimole of N-hydroxyphthalimide and 0.05 millimole of acetylacetonatomanganese(II) Mn(AA)$_2$. The resultant mixture was stirred at a temperature 70° C. for 6 hours in an oxygen atmosphere. As a result, durene was transformed into 2,4,5-trimethylbenzoic acid (yield 36%) with a transformation rate of 98 percent.

Example E26

A mixture of 10 millimoles of durene, 1 millimole of N-hydroxyphthalimide, 0.05 millimole of acetylacetonatoiron(III) Fe(AA)$_3$ and 25 milliliters of acetic acid was stirred at 70° C. for 3 hours in an oxygen atmosphere. Thus, durene was transformed into 2,4,5-trimethylbenzoic acid (yield 44%) with a transformation rate of 86 percent.

Example E27

To 25 milliliters of a mixture of acetonitrile and acetic acid (4:1) were added 10 millimoles of mesitylene, 1 millimole of N-hydroxyphthalimide and 0.05 millimole of acetylacetonatocobalt(II) Co(AA)$_2$. The resultant mixture was stirred at 70° C. for 3 hours in an oxygen atmosphere. Mesitylene was transformed into 3,5-dimethylbenzoic acid (yield 63%) with a transformation rate of 86 percent.

Example E28

A mixture of 10 millimoles of 3-ethyltoluene, 1-millimole of N-hydroxyphthalimide, 0.05 millimole of copper acetate (Cu(OAc)2) and 25 milliliters of acetonitrile was stirred, in an oxygen atmosphere, at 75° C. for six hours. As a result, 3-ethyltoluene was transformed into m-methylacetophenone (yield 57%) and 3-ethylbenzoic acid (yield 7%) with a transformation rate of 90 percent.

Example E29

To 25 milliliters of acetic acid were added 10 millimoles of 3-ethyltoluene, 1 millimole of N-hydroxyphthalimide and 0.05 millimole of acetylacetonatocobalt(II) Co(AA)$_2$. The resultant mixture was stirred, in an oxygen atmosphere, at 75° C. for six hours. With a transformation rate of 93 percent, 3-ethyltoluene was transformed into m-methylacetophenone (yield 55%) and 3-ethylbenzoic acid (yield 6%).

Example E30

A mixture of 10 millimoles of 4-ethyltoluene, 1 millimole of N-hydroxyphthalimide, 0.05 millimole of acetylacetonatocobalt(II) Co(AA)$_2$ and 25 milliliters of acetonitrile was stirred at 75° C. for 6 hours in an oxygen atmosphere. As a result, 4-ethyltoluene was transformed, with a transformation rate of 99 percent, into p-methylacetophenone (yield 66%) and 4-ethylbenzoic acid (yield 10%).

Example E31

To 25 milliliters of acetic acid were added 10 millimoles of 4-ethyltoluene, 1 millimole of N-hydroxyphthalimide and 0.05 millimole of acetlacetonatocobalt(II) Co(AA)$_2$. The resultant mixture was stirred, in an oxygen atmosphere, at 80° C. for 6 hours. With a transformation rate of 96 percent, 4-ethyltoluene was transformed or converted into p-methylacetophenone (yield 52%) and 4-ethylbenzoic acid (yield 6%).

Example E32

A mixture of 10 millimoles of durene, 1 millimole of N-hydroxyphthalimide, 0.05 millimole of acetylacetonatocobalt(II) Co(AA)$_2$ and 25 milliliters of acetic acid was stirred, in an oxygen atmosphere, at room temperature (about 20° C.) for 12 hours. Durene was transformed, with a transformation rate of 100 percent, into 2,4,5-trimethylbenzoic acid (yield 93%).

Example E33

To 25 milliliters of a mixture of acetic acid and acetonitrile (1:20) were added 10 millimoles of durene, 1 millimole of N-hydroxyphthalimide and 0.05 millimole of acetylacetonatocobalt(II) Co(AA)$_2$. The resulting mixture was stirred at room temperature (about 20° C.) for 12 hours in an oxygen atmosphere. Then, durene was transformed into 2,4,5-trimethylbenzoic acid (yield 94%) with a transformation rate of 100 percent.

Example E34

In an oxygen atmosphere, a mixture of 10 millimoles of durene, 1 millimole of N-hydroxyphthalimide, 0.05 millimole of acetylacetonatocobalt(II) Co(AA)$_2$ and 25 milliliters of acetonitrile was stirred at room temperature (about 20° C.) for 3 hours. With a transformation rate of 98 percent, durene was transformed into 2,4,5-trimethylbenzoic acid (yield 93%) and 2,4,5-trimethylbenzaldehyde (yield 5%).

Example E35

To 25 milliliters of acetic acid were added 10 millimoles of mesitylene, 1 millimole of N-hydroxyphthalimide and 0.05 millimole of acetylacetonatocobalt (II) Co(AA)$_2$. The resultant mixture was stirred at room temperature (about 15° C.) for 18 hours in an oxygen atmosphere, and mesitylene was transformed into 3,5-dimethylbenzoic acid (yield 20%) and 3,5-dimethylbenzaldehyde (yield 30%) with a transformation rate of 60 percent.

Example E36

A mixture of 10 millimoles of mesitylene, 1 millimole of N-hydroxyphthalimide, 0.05 millimole of acetylacetonatocobalt(II) Co(AA)$_2$ and 25 milliliters of acetonitrile was stirred, in an oxygen atmosphere, at room temperature (about 15° C.) for 6 hours. With a transformation rate of 61%, mesitylene was transformed into 3,5-dimethylbenzoic acid (yield 23%) and 3,5-dimethylbenzaldehyde (yield 25%).

Example E37

To 25 milliliters of acetic acid were added 10 millimoles of toluene, 1 millimole of N-hydroxyphthalimide and 0.05 millimole of acetylacetonatocobalt(II) Co(AA)$_2$. The resultant mixture was stirred, in an oxygen atmosphere, at room temperature (about 15° C.) for 24 hours, and toluene was transformed, with a transformation rate of 71 percent, into benzoic acid (yield 66%) and benzaldehyde (yield 3%).

Example E38

A mixture of 10 millimoles of toluene, 1 millimole of N-hydroxyphthalimide, 0.05 millimole of cobalt acetate (Co(OAc)$_2$) and 25 milliliters of acetic acid was stirred at room temperature (about 15° C.) for 24 hours in an oxygen atmosphere. As a result, toluene was transformed into benzoic acid (yield 60%) and benzaldehyde (yield 3%) with a transformation rate of 72 percent.

Example E39

To 25 milliliters of acetic acid were added 10 millimoles of p-t-butyltoluene, 1 millimole of N-hydroxyphthalimide and 0.05 millimole of acetylacetonatocobalt(II) Co(AA)$_2$. The resultant mixture was stirred, in an oxygen atmosphere, at room temperature (about 15° C.) for 18 hours. With a transformation rate of 94 percent, p-t-butyltoluene was transformed into p-t-butylbenzoic acid (yield 71%) and p-t-butylbenzaldehyde (yield 2%).

Example F1

In an oxygen atmosphere, a mixture of 10 millimoles of fluorene, 1 millimole of N-hydroxyphthalimide, 0.05 millimole of acetylacetonatomanganese Mn(AA)$_3$ and 25 milliliters of benzonitrile was stirred at a temperature of 100° C. for six hours. Products in the reaction mixture were analyzed with gas chromatography, and fluorene was transformed into fluorenone (yield 28%) with a transformation rate of 32 percent.

Example F2

Ten (10) millimoles of fluorene, 1 millimole of N-hydroxyphthalimide and 0.05 millimole of acetylacetonatomanganese Mn(AA)$_2$ were added to 25 milliliters of benzonitrile. The resultant mixture was stirred in an oxygen atmosphere at a temperature of 100° C. for six hours. A product in the reaction mixture was analyzed by means of gas chromatography, and fluorene was transformed into fluorenone (yield 30%) with a transformation rate of 38 percent.

Example F3

A mixture of 10 millimoles of fluorene, 1 millimole of N-hydroxyphthalimide, 0.05 millimole of acetylacetonatovanadium V(AA)$_3$ and 25 milliliters of acetic acid was stirred, in an oxygen atmosphere, at a temperature of 90° C. for 6 hours. In analyzing a product in the reaction mixture by gas chromatography, fluorene was transformed into fluorenone (yield 48%) with a transformation rate of 54 percent.

Example F4

To 25 milliliters of acetic acid were added 10 millimoles of fluorene, 1 millimole of N-hydroxyphthalimide and 0.05 millimole of acetylacetonatocobalt Co(AA)$_2$. The resultant mixture was stirred in an oxygen atmosphere at a temperature of 90° C. for 6 hours, and as a result of analysis of a product in the reaction mixture with gas chromatography, fluorene was transformed into fluorenone (yield 44%) and fluorenol (yield 3%) with a transformation rate of 68 percent.

Example G1

In an oxygen atmosphere, a mixture of 10 millimoles of adamantane, 1 millimole of N-hydroxyphthalimide, 0.05 millimole of acetylacetonatozirconium(IV) Zr(AA)$_4$ and 25 milliliters of acetic acid was stirred at a temperature of 75° C. for 6 hours. With the use of liquid chromatography, product in the reaction mixture was analyzed, and adamantane was transformed into 1-adamantanol (yield 40%), 1,3-adamantanediol (yield 8%) and 2-adamantanone (yield 6%) with a transformation rate of 74 percent. One hundred (100) percent of N-hydroxyphthalimide remained.

Example G2

The reaction was carried out in the same manner as Example G1, except using 0.05 millimole of acetylacetonatotitanium(II) Ti(AA)$_2$ in lieu of acetylacetonatozirconium(IV) Zr(AA)$_4$. Adamantane was transformed, with a transformation rate of 55 percent, into 1-adamantanol (yield 33%), 1,3-adamantanediol (yield 6%) and 2-adamantanone (yield 6%). All (100%) of N-hydroxyphthalimide remained after the reaction.

Example G3

The reaction procedure of Example G1 was repeated except that 0.05 millimole of acetylacetonatochromium(III) Cr(AA)$_3$ was employed instead of acetylacetonatozirconium(IV) Zr(AA)$_4$. With a transformation rate of 57 percent, adamantane was transformed into 1-adamantanol (yield 33%), 1,3-adamantanediol (yield 2%) and 2-adamantanone (yield 6%). A hundred (100) percent of N-hydroxyphthalimide retained after the completion of the reaction.

Example G4

A reaction was carried out in the same manner as Example G1 except using 0.05 millimole of acetylacetonatomanganese(III) Mn(AA)$_3$ instead of acetylacetonatozirconium(IV) Zr(AA)$_4$. As a result, adamantane was transformed, with a transformation rate of 68 percent, into 1-adamantanol (yield 37%), 1,3-adamantanediol (yield 7%) and 2-adamantanone (yield 5%), and 85 percent of N-hydroxyphthalimide remained.

Example G5

The procedure of Example G1 was repeated except employing 0.05 millimole of acetylacetonatomanganese(II) Mn(AA)$_2$ instead of acetylacetonatozirconium(IV) Zr(AA)$_4$. As a result, adamantane was transformed, with a transformation rate of 67 percent, into 1-adamantanol (yield 39%), 1,3-adamantanediol (yield 6%) and 2-adamantanone (yield 5%). N-hydroxyphthalimide remained in a ratio of 91 percent.

Example G6

A reaction was conducted in the same manner as Example G1 except that 0.05 millimole of molybdic acid H$_2$MoO$_4$ was used instead of acetylacetonatozirconium(IV) Zr(AA)$_4$. Adamantane was transformed into 1-adamantanol (yield 49%), 1,3-adamantanediol (yield 15%) and 2-adamantanone (yield 7%) with a transformation rate of 79 percent. Eighty-nine (89) percent of N-hydroxyphthalimide remained after completion of the reaction.

Example G7

To 25 milliliters of acetic acid were added 10 millimoles of adamantane, 1 millimole of N-hydroxyphthalimide and 0.1 millimole of acetylacetonatochromium(IV) Cr(AA)$_4$. The resultant mixture was stirred in an oxygen atmosphere at 85° C. for six hours. With a transformation rate of 90 percent, adamantane was transformed into 1-adamantanol (yield 38%), 1,3-adamantanediol (yield 24%), 1,3,5-adamantanetriol (yield 4%) and 2-adamantanone (yield 8%). Further, 97 percent of N-hydroxyphthalimide remained after completion of the reaction.

Example G8

A mixture of 10 millimoles of adamantane, 1 millimole of N-hydroxyphthalimide, 0.1 millimole of acetylacetonatozirconium(IV) Zr(AA)$_4$ and 25 milliliters of acetic acid was stirred, in an oxygen atmosphere, at 85° C. for six hours. As a result, adamantane was transformed into 1-adamantanol (yield 34%), 1,3-adamantanediol (yield 26%), 1,3,5-adamantanetriol (yield 3%) and 2-adamantanone (yield 6%), while 88 percent of N-hydroxyphthalimide remained.

Example G9

To 25 milliliters of acetic acid were added 10 millimoles of cyclohexane, 1 millimole of N-hydroxyphthalimide and 0.05 millimole of acetylacetonatomanganese Mn(AA)$_3$. The resultant mixture was stirred in an oxygen atmosphere at 110° C. for six hours. In analyzing products in the reaction mixture with liquid chromatography, cyclohexane was transformed into adipic acid (yield 70%) and cyclohexanone (yield 5%) with a transformation rate of 85 percent. Seventy-seven (77) percent of N-hydroxyphthalimide remained.

Example G10

A mixture of 10 millimoles of fluorene, 1 millimole of N-hydroxyphthalimide, 0.05 millimole of acetylacetonatozirconium $Zr(AA)_4$, and 25 milliliters of acetic acid was stirred in an oxygen atmosphere at 90° C. for 6 hours. Products in the reaction mixture were analyzed with liquid chromatography, and as a result, fluorene was transformed into fluorenone (yield 42%) and fluorenol (yield 4%) with a transformation rate of 68 percent. After completion of the reaction, 67 percent of N-hydroxyphthalimide remained.

Example G11

To 25 milliliters of acetic acid were added 10 millimoles of cyclohexane, 1 millimole of N-hydroxyphthalimide, and 0.05 millimole of acetylacetonatocobalt $Co(AA)_2$, and the resultant mixture was stirred in an oxygen atmosphere at 110° C. for 6 hours. In analyzing products in the reaction mixture by liquid chromatography, cyclohexane was transformed, with a transformation rate of 76%, into cyclohexanone (yield 36%), cyclohexanol (yield 1%) and adipic acid (yield 29%). After completion of the reaction, 48 percent of N-hydroxyphthalimide remained.

Example G12

A mixture of 10 millimoles of fluorene, 1 millimole of N-hydroxyphthalimide, 0.05 millimole of acetylacetonatocobalt $Co(AA)_2$ and 25 milliliters of acetic acid was stirred in an oxygen atmosphere at 90° C. for 6 hours. Products in the reaction mixture were analyzed with liquid chromatography, and as a result, fluorene was transformed into fluorenone (yield 40%) and fluorenol (yield 4%) with a transformation rate of 59 percent. Forty-eight (48) percent of N-hydroxyphthalimide remained after completion of the reaction.

Example G13

To 25 milliliters of acetic acid were added 10 millimoles of adamantane, 1 millimole of N-hydroxyphthalimide and 0.05 millimole of acetylacetonatovanadium $V(AA)_3$. The resultant mixture was stirred in an oxygen atmosphere at 75° C. for 3 hours, and products in the reaction mixture were analyzed by liquid chromatography. As a result, adamantane was transformed, with a transformation rate of 94%, into adamantanol (yield 40%), adamantanediol (yield 25%), adamantanetriol (yield 2%) and adamantanone (yield 7%), while 49 percent of N-hydroxyphthalimide remained.

Example G14

A mixture of 10 millimoles of adamantane, 1 millimole of N-hydroxyphthalimide, 0.03 millimole of acetylacetonatovanadium $V(AA)_3$ and 25 milliliters of acetic acid was stirred in an oxygen atmosphere at 75° C. for 3 hours. As a result of analysis of products in the reaction mixture with liquid chromatography, adamantane was transformed into adamantanol (yield 42%), adamantanediol (yield 24%), adamantanetriol (yield 2%) and adamantanone (yield 7%) with a transformation rate of 89 percent. After completion of the reaction, 54 percent of adamantane remained.

Example G15

To 25 milliliters of acetic acid were added 10 millimoles of adamantane, 1 millimole of N-hydroxyphthalimide, and 0.03 millimole of phosphovanadomolybdic acid $PV_5MO_7O_{40}.30H2O$. The resultant mixture was stirred in an oxygen atmosphere at 75° C. for 3 hours, and products in the reaction mixture were analyzed with liquid chromatography. Adamantane was transformed, with a transformation rate of 57 percent, into adamantanol (yield 37%), adamantanediol (yield 7%), and adamantanone (yield 6%). Incidentally, 61 percent of N-hydroxyphthalimide remained after completion of the reaction.

Example G16

A mixture of 10 millimoles of adamantane, 1 millimole of N-hydroxyphthalimide, 0.03 millimole of phosphovanadotungstic acid $PV_4W_8O_{40}$. $30H_2O$ and 25 milliliters of acetic acid was stirred in an oxygen atmosphere at 75° C. for 3 hours. Products in the reaction mixture were analyzed with the use of liquid chromatography, and as a result, adamantane was transformed into adamantanol (yield 36%), adamantanediol (yield 7%), and adamantanone (yield 5%) with a transformation rate of 49 percent. Fifty nine (59) percent of N-hydroxyphthalimide remained after completion of the reaction.

Example H1

To 25 milliliters of acetonitrile were added 1.08 grams (20 millimoles) of butadiene, 0.26 gram (1.6 millimoles) of N-hydroxyphthalimide and 0.03 gram (0.12 millimole) of acetylacetonatocobalt $Co(AA)_2$. The resultant mixture was stirred in an oxygen atmosphere at 60° C. for 6 hours. A gas chromatographic analysis of products in the reaction mixture indicated that butadiene was transformed, with a transformation rate of 35 percent, into 2-buten-1,4-diol (butadiene-based selectivity 63%, yield 22%), and 1-buten-3,4-diol (butadiene-based selectivity 23%, yield 8%). A selectivity for the alcohols was 86 percent.

Example H2

A mixture of 1.06 grams (20 millimoles) of acrylonitrile, 0.26 gram (1.6 millimoles) of N-hydroxyphthalimide, 0.03 gram (0.12 millimole) of acetylacetonatocobalt $Co(AA)_2$ and 25 milliliters of methanol was stirred in an oxygen atmosphere at 50° C. for 3 hours. In analyzing products in the reaction mixture with gas chromatography, acrylonitrile was transformed into 1,1-dimethoxypropionitrile (yield 99%) with a transformation rate of 99 percent.

Example H3

To 25 milliliters of methanol were added 1.72 grams (20 millimoles) of methyl acrylate, 0.26 gram (1.6 millimoles) of N-hydroxyphthalimide and 0.03 gram (0.12 millimole) of acetylacetonatocobalt $Co(AA)_2$. The resultant mixture was stirred in an oxygen atmosphere at 50° C. for three hours, and products in the reaction mixture were analyzed with gas chromatography. As a result, methyl acrylate was transformed, with a transformation rate of 99 percent, into methyl 1,1-dimethoxyprpionate in a yield of 99 percent.

We claim:

1. An oxidation catalytic system which comprises;

an imide compound shown by the following formula (1)

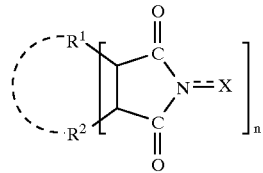

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring, and the aromatic or non-aromatic ring formed by $R^1$ and $R^2$ may have 1 or 2 of an imide unit shown by the following formula

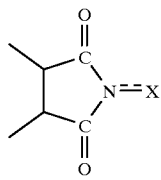

; and X represents an oxygen atom or a hydroxyl group; and n denotes an integer of 1 and a co-catalyst comprising an element selected from the group consisting of Group 2A elements of the Periodic Table of Elements, transition metals and Croup 3B elements of the Periodic Table of Elements, with a proviso that said co-catalyst is other than phosphovanadomolybdic acid and tetraphenylporphyrinato manganese (III) chloride for epoxidation of an alkene.

2. An oxidation catalytic system according to claim 1, wherein $R^1$ and $R^2$ in the imide compound of the formula (1) together form an aromatic or non-aromatic 5- to 12-membered ring.

3. An oxidation catalytic system according to claim 1, wherein $R^1$ and $R^2$ in the imide compound of the formula (1) together form a cycloalkane ring, a cycloalkene ring, a bridged hydrocarbon ring or an aromatic ring, each of which may have a substituent.

4. An oxidation catalytic system according to claim 1, wherein the imide compound shown by the formula (1) is a compound shown by any of the following formulae (1a) to (1f)

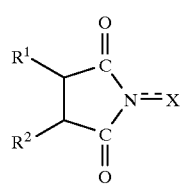

(1a)

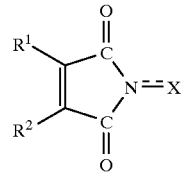

(1b)

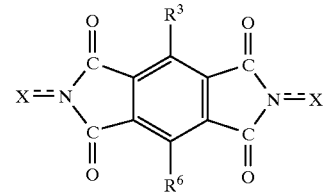

(1c)

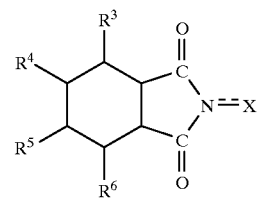

(1d)

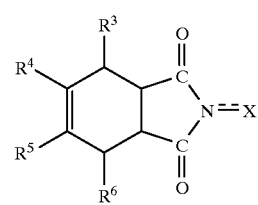

(1e)

(1f)

wherein $R^3$, $R^4$, $^5$ and $R^6$ represent, the same or different, a hydrogen atom, an alkyl group, a hydroxyl group, an alkoxy group, a carboxyl group, an alkoxy-carbonyl group, an acyl group, a nitro group, a cyano group, an amino group, or a halogen atom; and $R^1$, $R^2$, and X have the same meanings as defined above.

5. An oxidation catalytic system according to claim 1, wherein the imide compound of the formula (1) is at least one compound selected from the group consisting of N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide, N-hydroxytrimellimide, N,N'-dihydroxypyromellitimide and N,N'-dihydroxynaphthalenetetracarboximide.

6. An oxidation catalytic system according to claim 1, wherein said co-catalyst is a transition metal compound containing an element selected from the group consisting of Group 3A elements, Group 4A elements, Group 5A elements, Group 6A elements, Group 7A elements, Group 8 elements, Group 1B elements and Group 2B elements of the Periodic Table of Elements, or a boron compound.

7. An oxidation catalytic system according to claim 1, wherein said co-catalyst is a compound containing at least one element selected from the group consisting of Group 4A elements, Group 5A elements, Group 6A elements, Group 7A elements, Group 8 elements and Group 1B elements of the Periodic Table of Elements.

8. An oxidation catalytic system according to claim 1, wherein said co-catalyst is at least one member selected from the group consisting of oxides, salts of organic acids, salts of inorganic acids, halides, complexes, and isopolyacids or salts thereof.

9. An oxidation catalytic system according to claim 1, wherein said co-catalyst contains an element selected from the group consisting of lanthanoids, Ti, Zr, V, Cr, Mo, W, Mn, Fe, Ru, Co, Rh, Ni and Cu.

10. An oxidation catalytic system according to claim 1, wherein said system comprises a combination of the imide compound of the formula (1), and the co-catalyst containing at least one element selected from Group 4A elements, Group 6A elements and Group 7A elements of the Periodic Table of Elements.

11. An oxidation catalytic system according to claim 1, wherein said system comprises a combination of the imide compound of the formula (1), and the co-catalyst containing a Group 1B element of the Periodic Table of Elements.

12. An oxidation catalytic system according to claim 1, wherein said system comprises the imide compound of the formula (1), a compound containing a Group 7A element of the Periodic Table of Elements, and a compound containing a Group 8 element of the Periodic Table of Elements.

13. An oxidation catalytic system according to claim 12, wherein said compound containing the Group 7A element is a manganese compound, and said compound containing the Group 8 element is an iron compound.

14. An oxidation catalytic system according to claim 12, wherein a relative ratio of the compound containing the Group 8 element of the Periodic Table of Elements is 0.1 to 20 moles to 1 mole of the compound containing the Group 7A element of the Periodic Table of Elements.

15. An oxidation catalytic system according to claim 1, wherein a relative ratio of the co-catalyst to 1 mole of the imide compound of the formula (1) is 0.001 to 10 moles.

16. An oxidation catalytic system according to claim 1, wherein a relative ratio of the co-catalyst to 1 mole of the imide compound of the formula (1) is not greater than 0.1 mole.

17. A process for oxidation which comprises the step of contacting, with oxygen, one substrate selected from a cycloalkane, a cycloalkene, a polycyclic hydrocarbon containing a methylidyne group as a constitutive unit of a ring except for adamantane, an aromatic compound having at least one alkyl group and a conjugate compound, in the presence of an oxidation catalyst comprising an imide compound shown by the following formula (1)

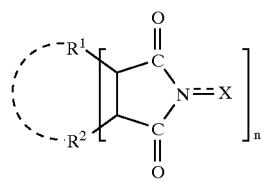

(1)

wherein $R^1$ and $R_2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring, and the aromatic or non-aromatic ring formed by $R^1$ and $R^2$ may have 1 or 2 of an imide unit shown by the following formula

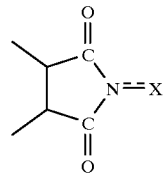

; and X represents an oxygen atom or a hydroxyl group, and n denotes an integer of 1, and a co-catalyst containing an element selected from the group consisting of Group 2A elements of the Periodic Table of Elements, transition metals, and Group 3B elements of the Periodic Table of Elements, with a proviso that when the substrate ia an aromatic compound having a hydroxyl group in a benzyl position, the co-catalyst is not phosphovanadomolybdic acid and tetraphenylporphyrinato manganese (III) chloride for epoxidation of an alkene.

18. A process according to claim 17, wherein oxidation is conducted in the coexistence of at least one co-catalyst selected from oxides, salts of organic acids, salts of inorganic acids, halides, complexes, and heteropolyacids or salts thereof.

19. A process according to claim 17, wherein the polycyclic hydrocarbon is a bridged cyclic hydrocarbon or a terpene each having at least one methylidyne group in a bridgehead position, or a condensed polycyclic hydrocarbon having at least one methylidyne group in a junction position of adjacent rings.

20. A process according to claim 17, wherein the polycyclic hydrocarbon is a hydrocarbon having plural methylidyne groups and containing 2 to 4 rings.

21. A process according to claim 17, wherein an adamantane component containing at least one component selected from an adamantanemonool, an adamantanediol and an adamantanetriol is allowed to contact with oxygen in the presence of the oxidation catalyst, for the formation of an adamantanepolyol which has been further hydroxylated.

22. A process according to claim 21, wherein a content of the adamantanemonool, adamantanediol or adamantanetriol is 5 mole percent or more based on the total of the adamantane component.

23. A process for oxidation which comprises the step of contacting a substrate with oxygen in the presence of an oxidation catalytic system comprising;

an imide compound shown by the following formula (1)

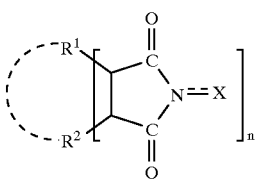

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R_2$ may together form a double bond or an aromatic or non-aromatic ring, and the aromatic or non-aromatic ring formed by $R^1$ and $R^2$ may have 1 or 2 of an imide unit shown by the following formula

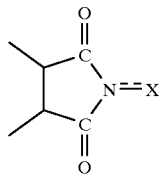

; and X represents an oxygen atom or a hydroxyl group; and n denotes an integer of 1, and a co-catalyst containing an element selected from the group consisting of Group 2A elements of the Periodic Table of Elements, transition metals, and Group 3B elements of the Periodic Table of Elements, with a proviso that when the substrate is an aromatic compound having a hydroxyl group in a benzyl position, the co-catalyst is not phosphovanadomolybdic acid and tetraphenylporphyrinato manganese (III) chloride, and that the substrate is an alkene.

24. A process according to claim 23, wherein said co-catalyst is at least one member selected from oxides, salts of organic acids, salts of inorganic acids, halides, complexes and heteropolyacids or salts thereof.

25. A process according to claim 23, wherein said substrate is (a) a cycloalkane, (b) a cycloalkene, (c) a polycyclic hydrocarbon having a methylidyne group as a constitutive unit of a ring, (d) an aromatic compound having a methyl group or a methylene group in an adjacent position with respect to an aromatic ring, or (e) a conjugate compound.

26. A process according to claim 25, wherein the cycloalkane is a compound having a 3- to 30-membered cycloalkane ring.

27. A process according to claim 23, wherein a compound having a 3- to 30-membered cycloalkane ring is oxidized with oxygen in the presence of the oxidation catalytic system, for the formation of a corresponding dicarboxylic acid or a cycloalkanone.

28. A process according to claim 25, wherein the polycyclic hydrocarbon is adamantane or its derivative.

29. A process according to claim 23, wherein a polycyclic hydrocarbon is oxidized with molecular oxygen in the presence of the oxidation catalytic system, for the formation of a compound introduced with a hydroxyl group.

30. A process according to claim 23, wherein an adamantane component selected from adamantane and its derivatives is allowed to contact with oxygen in the presence of the oxidation catalytic system, for the formation of an adamantanepolyol introduced with hydroxyl groups in plural bridgehead positions.

31. A process according to claim 25, wherein the compound (d) is an aromatic compound having at least one alkyl group.

32. A process according to claim 25, wherein the compound (d) has an aromatic heterocyclic ring, or an aromatic hydrocarbon ring having 6 to 14 carbon atoms.

33. A process according to claim 25, wherein the compound (d) is an aromatic hydrocarbon having at least one methyl group.

34. A process according to claim 23, wherein an aromatic compound having at least one methyl group is allowed to contact with oxygen in the presence of the oxidation catalytic system, for the formation of an aromatic compound having a carboxyl group.

35. A process according to claim 25, wherein the compound (e) is a conjugate diene, an α,β-unsaturated nitrile or a compound shown by the following formula

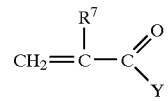

wherein $R^7$ represents a hydrogen atom or a methyl group; and Y represents —$OR^8$ or —$NR^9R^{10}$, where $R^8$ denotes a hydrogen atom, an alkyl group, an aryl group, a cycloalkyl group, a hydroxyalkyl group or a glycidyl group, and where $R^9$ and $R^{10}$ independently represent a hydrogen atom, an alkyl group or a hydroxyalkyl group.

36. A process according to claim 25, wherein the conjugate compound (e) is butadiene, isoprene, (meth) acrylonitrile, (meth)acrylic acid, (meth)acrylate, or (meth) acrylamide.

37. A process according to claim 23, wherein the imide compound of the formula (1) is used in a ratio of 0.001 to 1 mole relative to 1 mole of the substrate.

38. A process according to claim 23, wherein the co-catalyst is used in a ratio of 0.0001 to 0.7 mole relative to 1 mole of the substrate.

39. A process which comprises the step of contacting a substrate with oxygen in the presence of an oxidation catalytic system comprising;

an imide compound shown by the following formula (1)

(1)

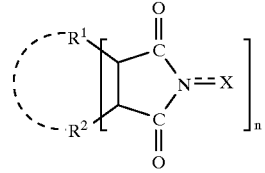

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl groups or an acyl group, or $R^1$ and $R^2$ may together form a double bond or an aromatic or non-aromatic ring, and the aromatic or non-aromatic ring formed by $R^1$ and $R^2$ may have 1 or 2 of an imide unit shown by the following formula

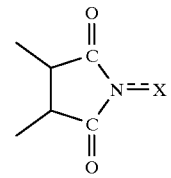

; and X represents an oxygen atom or a hydroxyl group; and n denotes an integer of 1, and a co-catalyst, except for phosphovanadomolybdic acid and tetraphenylporphyrinato manganese (III) chloride for epoxidation of an alkene, containing an element selected from the group consisting of Group 2A elements of the Periodic Table of Elements, transition metals and Group 3B elements of the Periodic Table of Elements, for the production of a ketone, an alcohol, an aldehyde or a carboxylic acid each corresponding to the substrate.

40. An oxidation catalytic system comprising formula (1):

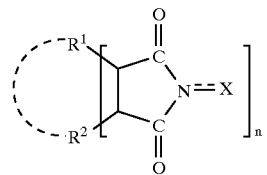 (1)

wherein $R^1$ and $R^2$ independently represent a hydrogen atom, a halogen atom, and alkyl group, am aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring, and the aromatic or non-aromatic ring formed by $R^1$ and $R^2$ may have 1 or 2 of an imide unit shown by the following formula

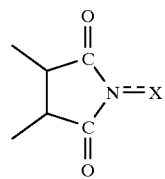

; and X represents an oxygen atom or a hydroxyl qroup; and n denotes an integer of 1, wherein said imide compound is a N-hydroxyimide or N-oxyimide compound corresponding to a polycarboxylic anhydride, and a co-catalyst comprising an element selected from the group consisting of group 2A elements or the Periodic Table of Elements, transition metals and Group 3B elements of the Periodic Table of Elements, with a proviso that said co-catalyst is other than phosphovanadomolybdic acid and tetraphenylporphyrinato manganese (III) chloride for epoxidation of an alkene.

* * * * *